(12) United States Patent
Boruah et al.

(10) Patent No.: US 9,199,967 B2
(45) Date of Patent: Dec. 1, 2015

(54) SUBSTITUTED HETEROCYCLIC AMINE COMPOUNDS AS CHOLESTRYL ESTER-TRANSFER PROTEIN (CETP) INHIBITORS

(75) Inventors: Anima Boruah, Andhra Pradesh (IN); Shanavas Alikunju, Andhra Pradesh (IN)

(73) Assignee: Dr. Reddy's Laboratories Ltd., Hyderabad, Telangana (IN)

( * ) Notice: Subject to any disclaimer, the term of this patent is extended or adjusted under 35 U.S.C. 154(b) by 0 days.

(21) Appl. No.: 14/238,272

(22) PCT Filed: Aug. 17, 2012

(86) PCT No.: PCT/IB2012/002056
§ 371 (c)(1),
(2), (4) Date: Apr. 14, 2014

(87) PCT Pub. No.: WO2013/024358
PCT Pub. Date: Feb. 21, 2013

(65) Prior Publication Data
US 2014/0256724 A1    Sep. 11, 2014

Related U.S. Application Data

(60) Provisional application No. 61/557,065, filed on Nov. 8, 2011.

(30) Foreign Application Priority Data

Aug. 18, 2011 (IN) ............................ 2829/CHE/2011

(51) Int. Cl.
| | | |
|---|---|---|
| A61K 31/435 | (2006.01) |
| C07D 401/12 | (2006.01) |
| C07D 401/14 | (2006.01) |
| C07D 413/14 | (2006.01) |
| C07D 413/12 | (2006.01) |

(52) U.S. Cl.
CPC ............ *C07D 401/12* (2013.01); *C07D 401/14* (2013.01); *C07D 413/12* (2013.01); *C07D 413/14* (2013.01); *A61K 31/435* (2013.01)

(58) Field of Classification Search
CPC .. C07D 413/14; C07D 413/12; C07D 401/12; C07D 401/14; A61K 31/435
See application file for complete search history.

(56) References Cited

U.S. PATENT DOCUMENTS

| | | |
|---|---|---|
| 2,858,309 A | 10/1958 | Druey et al. |
| 2,965,643 A | 12/1960 | Druey et al. |
| 3,546,295 A | 12/1970 | Maravetz |
| 5,086,073 A | 2/1992 | White et al. |
| 5,260,331 A | 11/1993 | White et al. |
| 5,332,759 A | 7/1994 | Depreux et al. |
| 5,348,953 A | 9/1994 | Doherty et al. |
| 5,422,355 A | 6/1995 | White et al. |
| 5,456,923 A | 10/1995 | Nakamichi et al. |
| 5,474,989 A | 12/1995 | Hashimoto et al. |
| 5,482,967 A | 1/1996 | Natsugari et al. |
| 5,491,152 A | 2/1996 | Wilde et al. |
| 5,545,608 A | 8/1996 | Morimoto et al. |
| 5,807,885 A | 9/1998 | Gentile et al. |
| 5,856,347 A | 1/1999 | Hashiguchi et al. |
| 5,892,114 A | 4/1999 | Goldmann et al. |
| 5,977,170 A | 11/1999 | Commons et al. |
| 5,985,326 A | 11/1999 | Butler |
| 6,008,231 A | 12/1999 | Lebaut et al. |
| 6,008,362 A | 12/1999 | Commons et al. |
| 6,121,271 A | 9/2000 | Dollings et al. |

(Continued)

FOREIGN PATENT DOCUMENTS

| | | |
|---|---|---|
| AU | 660026 | 6/1995 |
| EP | 0298666 A2 | 1/1989 |

(Continued)

OTHER PUBLICATIONS

P.J. Barter et al., 47 Journal of the American College of Cardiology, 492-498 (2006).*

(Continued)

*Primary Examiner* — Alexander R Pagano
(74) *Attorney, Agent, or Firm* — Stites & Harbison, PLLC; Mandy W. Decker

(57) ABSTRACT

The present application relates to cycloalkylpyridin-2-amines derivates of formula (1) or stereoisomers thereof or pharmaceutically acceptable salts thereof. The present application also relates to the process for the preparation of compounds of formula (I). The present application further describes the compounds of formula (1) as cholesteryl ester-transfer protein (CETP) inhibitors. The present application further relates to pharmaceutical compositions comprising compounds of formula (1) or stereoisomers thereof or pharmaceutically acceptable salts thereof.

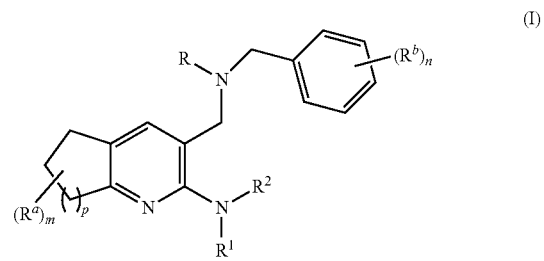

14 Claims, No Drawings

(56) References Cited

U.S. PATENT DOCUMENTS

| | | | |
|---|---|---|---|
| 6,147,089 A * | 11/2000 | DeNinno et al. | 514/313 |
| 6,218,431 B1 | 4/2001 | Schoen et al. | |
| 6,306,911 B1 | 10/2001 | Wachter et al. | |
| 6,350,786 B1 | 2/2002 | Albano et al. | |
| 6,407,111 B1 | 6/2002 | Bos et al. | |
| 6,432,987 B2 | 8/2002 | Gunther et al. | |
| 6,448,290 B1 | 9/2002 | Ohuchida et al. | |
| 6,488,922 B1 | 12/2002 | Damm et al. | |
| 6,489,478 B1 | 12/2002 | DeNinno et al. | |
| 6,498,172 B1 | 12/2002 | Cameron et al. | |
| 6,548,555 B1 | 4/2003 | Curatolo et al. | |
| 6,576,644 B2 | 6/2003 | Bi et al. | |
| 6,638,522 B1 | 10/2003 | Mulye | |
| 6,642,252 B2 | 11/2003 | Bisacchi et al. | |
| 6,710,089 B2 | 3/2004 | Sikorski et al. | |
| 6,713,499 B2 | 3/2004 | Flohr et al. | |
| 6,723,753 B2 | 4/2004 | Sikorski et al. | |
| 6,730,679 B1 | 5/2004 | Roy et al. | |
| 6,962,931 B2 | 11/2005 | Gumkowski et al. | |
| 7,008,640 B2 | 3/2006 | Watanabe et al. | |
| 7,012,081 B2 | 3/2006 | Krueger et al. | |
| 7,034,013 B2 | 4/2006 | Thompson et al. | |
| 7,037,528 B2 | 5/2006 | Kipp et al. | |
| 7,078,057 B2 | 7/2006 | Kerkhof | |
| 7,081,255 B2 | 7/2006 | Baert et al. | |
| 7,276,610 B2 | 10/2007 | Huang et al. | |
| 7,332,514 B2 | 2/2008 | Maeda et al. | |
| 7,459,470 B2 | 12/2008 | Ernst et al. | |
| 7,470,705 B2 | 12/2008 | Bell et al. | |
| 7,579,365 B2 | 8/2009 | Nickel et al. | |
| 7,619,096 B2 | 11/2009 | Beadle et al. | |
| 7,737,295 B2 | 6/2010 | Ali et al. | |
| 7,781,443 B2 | 8/2010 | Kubota et al. | |
| 8,030,359 B2 | 10/2011 | Geers et al. | |
| 8,158,640 B2 | 4/2012 | Kubota et al. | |
| 8,389,011 B2 | 3/2013 | Crew et al. | |
| 8,604,055 B2 * | 12/2013 | Baruah et al. | 514/312 |
| 2002/0052363 A1 | 5/2002 | Dinsmore et al. | |
| 2002/0177587 A1 | 11/2002 | Bi et al. | |
| 2002/0193283 A1 | 12/2002 | Dinsmore et al. | |
| 2003/0054037 A1 | 3/2003 | Babcock et al. | |
| 2003/0072801 A1 | 4/2003 | Curatolo et al. | |
| 2003/0104063 A1 | 6/2003 | Babcock et al. | |
| 2003/0114454 A1 | 6/2003 | Sikorski et al. | |
| 2003/0170309 A1 | 9/2003 | Babcock et al. | |
| 2003/0198674 A1 | 10/2003 | Curatolo et al. | |
| 2004/0039018 A1 | 2/2004 | Ruggeri | |
| 2004/0053842 A1 | 3/2004 | Nguyen et al. | |
| 2004/0176446 A1 | 9/2004 | Alonso-Alija et al. | |
| 2004/0185102 A1 | 9/2004 | Friesen et al. | |
| 2005/0038007 A1 | 2/2005 | Curatolo et al. | |
| 2005/0049239 A1 | 3/2005 | Huang et al. | |
| 2005/0059810 A1 | 3/2005 | Maeda et al. | |
| 2005/0153964 A1 | 7/2005 | Leach et al. | |
| 2006/0178514 A1 * | 8/2006 | Baruah et al. | 544/406 |
| 2009/0118328 A1 | 5/2009 | Friesen et al. | |
| 2009/0227580 A1 | 9/2009 | Kishida et al. | |
| 2009/0239865 A1 | 9/2009 | Chang et al. | |
| 2010/0249148 A1 | 9/2010 | Ohgiya et al. | |
| 2011/0189210 A1 | 8/2011 | Okamoto et al. | |

FOREIGN PATENT DOCUMENTS

| | | |
|---|---|---|
| EP | 0585500 A1 | 3/1994 |
| EP | 0604798 A1 | 7/1994 |
| EP | 1108426 A2 | 6/2001 |
| EP | 1741424 A2 | 1/2007 |
| GB | 2087390 A | 5/1982 |
| JP | 01104052 H | 4/1989 |
| JP | 07285962 H | 10/1995 |
| JP | 0892224 H | 4/1996 |
| JP | 0892225 H | 4/1996 |
| JP | 11209366 H | 8/1999 |
| WO | 93/00332 | 1/1993 |
| WO | 94/05648 | 3/1994 |
| WO | 96/02509 A1 | 2/1996 |
| WO | 98/57925 | 12/1998 |
| WO | 98/57927 | 12/1998 |
| WO | 98/57928 | 12/1998 |
| WO | 01/00623 A1 | 1/2001 |
| WO | 01/02350 A2 | 1/2001 |
| WO | 01/22954 A2 | 4/2001 |
| WO | 02/22584 A1 | 3/2002 |
| WO | 02/068417 A2 | 9/2002 |
| WO | 03/030909 A1 | 4/2003 |
| WO | 03/063832 A1 | 8/2003 |
| WO | 2004/073709 A1 | 9/2004 |
| WO | 2004/078128 A2 | 9/2004 |
| WO | 2004/078169 A1 | 9/2004 |
| WO | WO 2006073973 A2 * | 7/2006 |
| WO | 2007/075194 A1 | 7/2007 |
| ZA | 9204659 | 3/1993 |

OTHER PUBLICATIONS

P.J. Barter et al., 32 Trends in Pharmacological Sciences, 694-699 (2011).*

M. Mitka, 305 JAMA, 136-137 (2011).*

J.A. Sikorski, 49 Journal of Medicinal Chemistry, 1-22 (2006).*

International Search Report and Written Opinion dated May 8, 2013, for corresponding International Patent Application No. PCT/IB2012/002056.

Gordon et al., "High-Density Lipoprotein Cholesterol and Cardiovascular Disease—Four Prospective American Studies", Circulation, Jan. 1989, pp. 8-15, vol. 79—issue No. 1, American Heart Association.

Despres et al., "HDL-cholesterol as a marker of coronary heart disease risk: the Quebec cardiovascular study", Atherosclerosis, 2000, pp. 263-272, vol. 153, Elsevier Science Ireland Ltd.

International Search Report and Written Opinion dated Mar. 27, 2014, for corresponding International Patent Application No. PCT/IB2013/002909.

Tae-Wan Kim et al., "Modified Release of Coated Sugar Spheres Using Drug-Containing Polymeric Dispersions", Arch Pharm Res, 2007, pp. 124-130, vol. 30—issue No. 1.

Tae-Wan Kim et al., "Characterization of Dual Layered Pellets for Sustained Release of Poorly Water-Soluble Drug", Chem. Pharm. Bull., Jul. 2007, pp. 975-979, vol. 55-issue No. 7, Pharmaceutical Society of Japan.

Toshiya Kai et al., "Oral Absorption Improvement of Poorly Soluble Drug Using Solid Dispersion Technique", Chem. Pharm. Bull., Mar. 1996, pp. 568-571, vol. 44—issue No. 3, Pharmaceutical Society of Japan.

Tomaz Einfalt et al., "Methods of amorphization and investigation of the amorphous state", Acta Pharm., 2013, pp. 305-334, vol. 63.

International Search Report and Written Opinion dated Feb. 25, 2013, for corresponding International Patent Application No. PCT/IB2012/002435.

Al-Dabbagh and Smith, "Species Differences in Oxidative Drug Metabolism: Some Basic Considerations", Archives of Toxicology, 1984, pp. 219-231, Suppl. 7, Springer-Verlag.

Hans Bundgaard, "Design of prodrugs: Bioreversible derivatives for various functional groups and chemical entities", Design of Prodrugs, 1985, p. 1, Elsevier Science Publishers B.V. (Biomedical Division).

Richard B. Silverman, "Prodrugs and Drug Delivery Systems", The Organic Chemistry of Drug Design and Drug Action, 1992, pp. 352-400, Academic Press, Inc.

Vippagunta et al., "Crystalline Solids", Advanced Drug Delivery Reviews, 2001, pp. 3-26, vol. 48, Elsevier Science B.V.

Extended European Search Report dated Jun. 22, 2010, for corresponding European Patent Application No. 06 77 4300.

Kerns and Di, "Permeability Structure Modification Strategies", Drug-like Properties: Concepts, Structure Design and Methods: from ADME to Toxicity Optimization, 2008, pp. 92-93, Elsevier Inc.

Goosen et al., "Physiochemical Characterization and Solubility Analysis of Thalidomide and Its N-Alkyl Analogs", Pharmaceutical Research, Jan. 1, 2002, pp. 13-19, vol. 19—issue No. 1, Plenum Publishing Corporation.

(56) References Cited

OTHER PUBLICATIONS

Fourie et al., "Percutaneous delivery of carbamazepine and selected N-Alkyl and N-hydroxyalkyl analogues", International Journal of Pharmaceutics, 2004, pp. 59-66, vol. 279, Elsevier B.V.

Edwards et al., "Nonpeptidic Inhibitors of Human Neutrophil Elastase. 7. Design, Synthesis, and in Vitro Activity of a Series of Pyridopyrimidine Trifluromethyl Ketones", Journal of Medicinal Chemistry, 1996, pp. 1112-1124, vol. 39—issue No. 5, American chemical Society.

Rautio et al., "Piperazinyalkyl prodrugs of naproxen improve in vitro skin permeation", European Journal of Pharmaceutical Sciences, 2000, pp. 157-163, vol. 11, Elsevier Science B.V.

Anzini et al., "Mapping and Fitting the peripheral Benzodiazepine Receptor Binding Site by Carboxamide Derivatives. Comparison of Different Approaches to Quantitative Ligand-Receptor Interaction Modeling", J. Med. Chem., 2001, pp. 1134-1150, vol. 44—issue No. 8, American Chemical Society.

Sculley and Hamilton, "Some Amide Derivatives of Certain Aminomethylpyridines", J. American Chem. Soc., Jul. 20, 1953, pp. 3400-3403, vol. 75.

Berge et al., "Pharmaceutical Salts", Review Article, Journal of Pharmaceutical Studies, Jan. 1977, p. 1-19, vol. 66—issue No. 1.

Derry E. V. Wilman, "Prodrugs in cancer chemotheraphy", Action Cancer Guest Lecture, Biochemical Society Transactions, 615th Meeting, Belfast, 1986, pp. 375-385, vol. 14.

Stella and Himmelstein, "Prodrugs: A Chemical Approach to Targeted Drug Delivery", Directed Drug Delivery—A Multidisciplinary Problem, 1985, pp. 247-267, Humana Press, Clifton, New Jersey.

Ali et al., "An Efficient and Facile Synthesis of 2-Chloro-3-formyl Quinolines from Acetanilides in Micellar Media by Vilsmeier-Haack Cyclisation", Letter, Synlett, 2001, pp. 251-253, issue No. 2, Thieme Stuttgart, New York.

John B. Paine III, "A Convenient Synthesis of Nicotinate Esters from 3-Cyanopyridones", J. Heterocyclic Chem., 1987, pp. 351-355, vol. 24.

Boatman et al., "Alkylations at the Methyl or α-Methylene Group of 6- or 4-Alkyl-3-cyano-2(1)-pyridones through Dianions", J. Organic Chemistry, Nov. 1965, pp. 3593-3597, vol. 30.

Cappelli et al., "Design, Synthesis, Structural Studies, Biological Evaluation, and Computational Simulations of Novel Potent AT1 Angiotensin II Receptor Antagonists Based on the 4-Phenylquinolines Structure", J. Med. Chem., 2004, pp. 2574-2586, vol. 47—issue No. 10, American Chemical Society.

Izumi et al., "1H-Imidazo[4,5-c]quinoline Derivatives as Novel potent TNF-α Suppressors: Synthesis and Structure-Activity Relationship of 1-, 2- and 4-Substituted 1H-imidazo[4,5-c]quinolines or 1H-imidazo[4,5-c]pyridines", Bioorganic & Medicinal Chemistry, 2003, pp. 2541-2550, vol. 11, Elsevier Science Ltd.

Yin and Buchwald, "Palladium-Catalyzed Intermolecular Coupling of Aryl Halides and Amides", Organic Letters, 2000, pp. 1101-1104, vol. 2—issue No. 8, American Chemical Society.

Robert Franzen, "The Suzuki, the Heck, and the Stille reaction—three versatile methods for the introduction of new C-C bonds on solid support", Can. J. Chem., 2000, pp. 957-962, vol. 78, NRC Canada.

Negishi et al., "Cyclic Carbopalladation. A Versatile Synthetic Methodology for the Construction of Cyclic Organic Compounds", Chemical Reviews, 1996, pp. 365-393, vol. 96—issue No. 1, American Chemical Society.

McGee, Jr. et al., "Fusicoccin Synthesis by Intramolecular [4+4] Photocycloaddition of 2-Pyridones: Stereocontrol of the Cycloaddition and Elaboration of the Pentacyclic Product", Paper, Synthesis, Jun. 18, 2001, pp. 1185-1196, issue No. 8, Georg Thieme Verlag Stuttgart, New York.

Bisgaier et al., "Use of flourescent cholesteryl ester microemulsions in cholesteryl ester transfer protein assays", Paper on Methodology, Journal of Lipid Research, 1993, pp. 1625-1634, vol. 34.

Epps et al., "Method for measuring the activities of cholesteryl ester transfer protein (lipid transfer protein)", Chemistry and Physics of Lipids, 1995, pp. 51-63, vol. 77, Elsevier Science Ireland Ltd.

International Search Report and Written Opinion dated Oct. 23, 2006, for corresponding International Patent Application No. PCT/US06/25427.

INPADOC/Family and Legal Status Search Results, obtained from Dialog Database #345, Jun. 14, 2006, 19 pages.

Derwent World Patent Index Search Results, obtained from Delphion website (www.delphion.com), 5 pages.

* cited by examiner

SUBSTITUTED HETEROCYCLIC AMINE COMPOUNDS AS CHOLESTRYL ESTER-TRANSFER PROTEIN (CETP) INHIBITORS

This application is a National Stage Application under 35 U.S.C. §371 of PCT International Application No. PCT/IB2012/002056 filed Aug. 17, 2012, which claims the benefits of U.S. Provisional Application No. 61/557,065, filed on Nov. 8, 2011 and Indian Provisional Application No. 2829/CHE/2011, filed Aug. 18, 2011, all of which are hereby incorporated by reference in their entireties.

TECHNICAL FIELD

The present application relates to cycloalkylpyridin-2-amines derivates of formula (I) or stereoisomers thereof or pharmaceutically acceptable salts thereof.

BACKGROUND

Cholesteryl ester-transfer protein (CETP) is an important player in metabolism of lipoproteins such as, for example, a high density lipoprotein (HDL). CETP is a 70 kDa plasma glycoprotein that is physically associated with HDL particles. It facilitates the transport of cholesteryl ester from HDL to apolipoprotein B-containing lipoproteins. This transfer is accompanied by transfer of triglycerides in the opposite direction. Thus, a decrease in CETP activity can result in an increase in the level of HDL cholesterol and a decrease in the level of very low density lipoprotein (VLDL) and low density lipoprotein (LDL). CETP can therefore simultaneously affect the concentrations of pro-atherogenic (e.g., LDL) and anti-atherogenic (e.g., HDL) lipoproteins.

Clinical studies in humans have shown that inhibitors of CETP can be effective in elevating HDL levels by 30-110%. Further, epidemiological studies have shown that low high-density lipoprotein cholesterol (HDL-C) levels is a powerful risk factor for coronary artery disease (CAD). See generally, Gordon et al., Circulation, 79, pp. 8-15, 1989; Despres et al., Atherosclerosis 153: 263-272, 2000. Elevating HDL-C has been shown to decrease this risk and it is estimated that each 1 mg/dl (0.02 mmol/1) elevation of HDL-C is associated with a 2-3% reduction in coronary heart disease (CHD) risk, a magnitude comparable to that for low density lipoprotein (LDL) lowering.

It is believed that the anti-atherogenic role of HDL is in part due to its ability to promote the efflux of free cholesterol from cells and to transport it to the liver, a process termed reverse cholesterol transport. HDL could protect against atherosclerosis by several other mechanisms. For example, several studies have shown that HDL to have antioxidant and anti-inflammatory effects. Oxidative products of lipid metabolism induce inflammatory cell recruitment in vascular cells. HDL particles carry enzymes that retard LDL oxidation, including paraoxonase, platelet-activating factor acetylhydrolase, and lecithin-cholesterol acyltransferase. These enzymes degrade pro-inflammatory, oxidized phospholipids, limiting their accumulation in LDL. In addition, apoA-I can bind oxidized lipids and remove them from LDL. Further, HDL also can act as a carrier vehicle for small molecules, including bacterial lipopolysaccharide (LPS) thus regulating the inflammatory effects of LPS. In animal models of endotoxic shock, HDL attenuates organ injury and adhesion molecule expression. Thus elevating HDL is not only anti-atherogenic but it could also potentially be anti-inflammatory.

Elevation of HDL by CETP inhibition has been described in the art.

However, no CETP inhibitors are currently being marketed. Further, other existing therapies such as, for example, HDL-elevating therapies and anti-atherosclerosis therapies have limitations including serious tolerance issues. Thus, there is a present need to find alternative therapies including methods of preventing or treating conditions or diseases associated with lipoprotein metabolism such as, for example, atherosclerosis.

SUMMARY

Accordingly, the present application relates to cycloalkylpyridin-2-amine derivatives of the general formula (I):

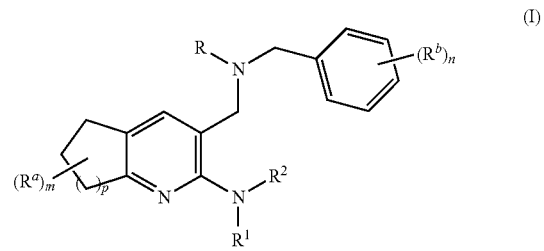

wherein,
R represents

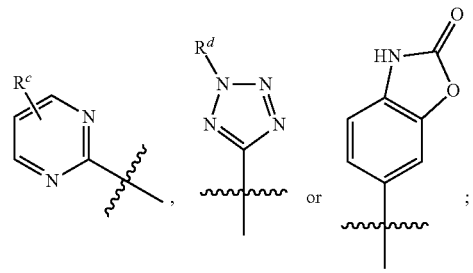

$R^1$ and $R^2$ are independently selected from hydrogen, acyl, haloalkyl, —$(CHR^e)_qR^3$, an optionally substituted group selected from alkyl or cycloalkyl, wherein optional substituent, in each occurrence, is independently selected from halogen, cyano, hydroxyl, an alkyl, a haloalkyl or an alkoxy;

$R^3$ is a group selected from alkoxy, haloalkoxy, cycloalkyl, aryl, heterocyclyl or heteroaryl, wherein $R^3$ is optionally substituted with a group selected from halogen, cyano, hydroxyl, alkyl, haloalkyl or alkoxy;

$R^a$, in each occurrence, is independently selected from cyano, hydroxy, alkyl, haloalkyl or alkoxy;

$R^b$, in each occurrence, is independently selected from halogen, alkyl, haloalkyl, hydroxy, alkoxy or haloalkoxy;

$R^c$ is independently selected from hydrogen, cyano, halogen, —C(=O)—$R^f$, —$CONR^gR^h$, —C(=O)—CH=CH—$NR^iR^j$, an optionally substituted group selected from cycloalkyl, aryl, heteroaryl or heterocyclyl ring, wherein the optional substituent, in each occurrence, is selected independently from hydrogen, halogen, cyano, hydroxyl, alkyl, haloalkyl, alkoxy, alkoxyalkyl or haloalkoxy;

$R^d$ is selected from hydrogen or alkyl;

R$^e$, in each occurrence, is independently selected from hydrogen, alkyl or alkoxy;

R$^f$ is selected from hydrogen or alkyl;

R$^g$, R$^h$, R$^i$ and R$^j$, independently represents hydrogen or alkyl;

m is 0, 1 or 2;

n is 0, 1, 2 or 3;

p is 1 or 2; and q is 0, 1, 2, 3, 4 or 5.

The present application also relates to the process for the preparation of compounds of formula (I).

The present application further describes the compounds of formula (I) as cholesteryl ester-transfer protein (CETP) inhibitors.

The present application further relates to pharmaceutical compositions comprising compounds of formula (I) or stereoisomers thereof or pharmaceutically acceptable salts thereof.

DETAILED DESCRIPTION

The present application will be described in more detail below:

'Alkyl' group refers to a linear or branched alkyl group with 1 to 10 carbon atoms. Exemplary alkyl groups include, but are not limited to, methyl, ethyl, n-propyl, iso-propyl, n-butyl, iso-butyl, t-butyl, n-pentyl, iso-pentyl, hexyl, heptyl, octyl and the like.

'Alkoxy' group refers to an —O-(alkyl) group, wherein alkyl group is as defined above. Exemplary alkoxy groups include methoxy, ethoxy, n-propoxy, iso-propoxy, n-butoxy, iso-butoxy, t-butoxy, and the like. Unless otherwise specified, an alkoxy group has from 1 to 10 carbon atoms.

'Alkoxyalkyl' refers to an alkoxy substituted alkyl group, wherein alkoxy and alkyl groups are as defined above. Typically, the alkoxy group can have from 1 to 10 carbon atoms, and the alkyl group can have from 1 to 10 carbon atoms. Exemplary alkoxyalkyl groups include, but are not limited to, ethoxymethyl, propoxyethyl, ethoxybutyl and the like.

'Acyl' group refers to alkyl-CO— group, wherein alkyl group is as defined above. Acyl group refers to an alkyl-linker moiety bonded to the CO group. Examples of acyl groups include, but are not limited to, acetyl, propionyl and the like. Acyl group includes formyl group also.

'Aryl' is a monocyclic or polycyclic aromatic ring system. Exemplary aryl groups include, but are not limited to, phenyl, naphthyl, and the like. Unless otherwise specified, an aryl group typically has from 6 to about 14 carbon atoms.

'Cycloalkyl' group refers to a cyclic alkyl group which may be mono, bicyclic, polycyclic, or a fused/bridged ring system. Exemplary cycloalkyl groups include, but are not limited to, cyclopropyl, cyclobutyl, cyclopentyl, cyclohexyl, cycloheptyl, cyclooctyl, and the like. Unless otherwise specified, a cycloalkyl group typically has from 3 to about 10 carbon atoms. Typical bridged cycloalkyl groups include, but are not limited to adamantyl, noradamantyl, bicyclo[1.1.0]butanyl, norbornyl(bicyclo[2.2.1]heptanyl), norbornenyl(bicyclo[2.2.1]heptanyl), norbornadienyl(bicyclo[2.2.1]heptadienyl), bicyclo[2.2.1]heptanyl, bicyclo[3.2.1]octanyl, bicyclo[3.2.1]octadienyl, bicyclo[2.2.2]octanyl, bicyclo[2.2.2]octenyl, bicyclo[2.2.2]octadienyl, bicyclo[5.2.0]nonanyl, bicyclo[4.3.2]undecanyl, tricyclo[5.3.1.1]dodecanyl and the like.

'Halogen or Halo' represents fluorine, chlorine, bromine, or iodine.

'Haloalkyl' means at least one halogen atom is substituted on an alkyl group. Both halogen and alkyl have the meaning as defined above. Representative examples of haloalkyl groups include, but are not limited to, fluoromethyl, chloromethyl, fluoroethyl, chloroethyl, difluoromethyl, trifluoromethyl, dichloroethyl, trichloroethyl and the like. Unless otherwise specified, a haloalkyl group typically has from 1 to 10 carbon atoms.

'Haloalkoxy' means at least one halogen atom is substituted on an alkoxy group, wherein alkoxy and halogen groups are as defined above. Exemplary haloalkoxy groups include, but not limited to, fluoromethoxy, chloromethoxy, trifluoromethoxy, trichloroethoxy, fluoroethoxy, chloroethoxy, trifloroethoxy, perfluoroethoxy (—OCF$_2$CF$_3$), trifluoro-t-butoxy, hexafluoro-t-butoxy, perfluoro-t-butoxy (—OC(CF$_3$)$_3$), and the like. Unless otherwise specified, an haloalkoxy group typically has from 1 to 10 carbon atoms.

'Heterocyclyl' is a saturated monocyclic or polycyclic ring system of 3 to 10 members having at least one heteroatom or heterogroup selected from —O—, —N—, —S—, —SO$_2$, or —CO. Exemplary heterocyclyl groups include, but not limited to, azetidinyl, oxazolidinyl, oxazolidinonly, isoxazolidinyl, imidazolidin-2-onyl, pyrrolidinyl, pyrrolidin-2-onyl, piperidinyl, piperazinyl, morpholinyl, thiomorpholinyl, thiomorpholine-1,1-dioxide, thiazolidinyl, 1,3-dioxolanyl, 1,4-dioxanyl, cyclopenta[b]pyridinyl, cyclopenta[d]pyrimidinyl and the like. Unless otherwise specified, a heterocyclyl group typically has from 3 to about 10 carbon atoms.

'Heteroaryl' is an unsaturated, aromatic or non-aromatic, monocyclic or polycyclic ring system of 3 to 10 members having at least one heteroatom or heterogroup selected from —O—, —N—, —S—, —SO$_2$, or —CO. Exemplary heteroaryl groups include, but not limited to, oxazolyl, isoxazolyl, thiazolyl, pyridinyl, pyrrolyl, pyrimidinyl, thiazinyl, pyrazinyl, pyrazolyl, tetrazolyl, imidazothiazolyl, indolizidinyl, indolyl, quinolinyl, quinoxalinyl, benzoxazolyl, benzoisoxazolyl, benzothiazolyl, benzodioxolyl, benzotriazolyl, indazolyl, quinoxalinyl, imidazolyl, quinolin-2(1H)-onyl, and the like. Unless otherwise specified, a heteroaryl group typically has from 3 to about 10 carbon atoms.

'(C$_1$-C$_{10}$)alcohol' represents '(C$_1$-C$_{10}$)alkyl-OH', wherein alkyl group is as defined above. Exemplary (C$_1$-C$_{10}$)alcohol includes methanol, ethanol, propanol, isopropanol, butanol, isobutanol and the like.

The Cholesteryl ester-transfer protein (CETP) may be an animal or a non-mammalian or mammalian protein, such as a human protein.

'Optionally substituted' means that the substitution is optional and therefore it is possible for the designated atom or molecule to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example, in formula (I) when a substituent is oxo (i.e., =O), then two hydrogens on the atom are replaced and when the substitution is fluoro, then one hydrogen on the atom is replaced and the like.

As used herein and in the appended claims, the singular forms "a", "an", and "the" include plural reference unless the context clearly indicates otherwise.

Unless defined otherwise, all technical and scientific terms used herein have the same meaning as commonly understood to one of ordinary skill in the art.

One or more compounds of formula (I) can be supplied in the form of a therapeutic composition that is within the scope of the present application.

'Salts' refer to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the application. The preparation of salts can be carried out using known methods.

For example, pharmaceutically acceptable salts of compounds contemplated herein may be synthesized by conventional chemical methods using a parent compound containing an acid residue. Generally, such salts may be prepared, for example, by making free base of the compounds and reacting with a stoichiometric quantity of the appropriate acid and vice-versa in water or in an organic solvent, or in a mixture of the two. Generally, non-aqueous media such as ether, ethyl acetate, ethanol, isopropanol or acetonitrile may be utilized. Examples of acid addition salts include, but are not limited to, mineral acid addition salts such as hydrochloride, hydrobromide, hydroiodide, sulphate, nitrate, phosphate, and organic acid addition salts such as acetate, maleate, fumarate, citrate, oxalate, succinate, tartrate, malate, mandelate, methanesulphonate and p-toluenesulphonate. Also included in present application are the isomeric forms and tautomers and the pharmaceutically-acceptable salts of compounds of formula (I). Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric, and galacturonic acids.

The term 'stereoisomers' is a general term used for all isomers of the individual molecules that differ only in the orientation of their atoms in space. Typically it includes mirror image isomers that are usually formed due to at least one asymmetric center (enantiomers). Where the compounds according to the present application possess one or more asymmetric centers and can thus occur as racemates, racemic mixtures, single enantiomers, diastereomeric mixtures and individual diastereomers. Also certain individual molecules may exist as geometric isomers (cis/trans). Similarly, certain compounds of this application may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present application.

For any particular compound disclosed herein, any general structure presented also encompasses all conformational isomers, regioisomers and tautomers that may arise from a particular set of substituents.

As used herein, the term 'subject' or 'patient' means mammals, such as humans and other animals, including horses, dogs, cats, rats, mice, sheep, pigs, etc. In exemplary embodiments, the subject may include subjects for which treatment and/or prevention of the conditions described herein would be beneficial.

For ease of reference, in this application it will be described in terms of administration to human subjects. It will be understood, however, that such descriptions are not limited to administration to humans, but will also include administration to other animals unless explicitly stated otherwise.

A 'therapeutically effective amount' is the amount of compound that is effective in obtaining a desired clinical outcome in the treatment of a specific disease.

The terms 'treating' or 'to treat' means to alleviate symptoms, eliminate the causation either on a temporary or permanent basis, or to prevent or slow the appearance of symptoms. The term 'treatment' includes alleviation, elimination of causation of or prevention of any of the diseases or disorders described above. Besides being useful for human treatment, these combinations are also useful for treatment of other mammals, including horses, dogs, cats, rats, mice, sheep, pigs, etc.

Terms such as "about," "substantially," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

As used herein, "comprising" means the elements recited, or their equivalent in structure or function, plus any other element or elements which are not recited. The terms "having," "including," and "comprised of" are also to be construed as open ended unless the context suggests otherwise.

The compounds described herein are typically administered in admixture with one or more pharmaceutically acceptable excipients or carriers in the form of a pharmaceutical composition. A 'composition' may contain one compound or a mixture of compounds. A 'pharmaceutical composition' is any composition useful or potentially useful in producing at least one physiological response in a subject to which such pharmaceutical composition is administered.

Reference will now be made in detail to the embodiments of the present application, one or more examples of which are set forth below. Each example is provided by way of explanation of the invention, and not by way of limitation of the invention. In fact, it will be apparent to those skilled in the art that various modification and variations can be made in the present application without departing from the scope or spirit of the invention. For instance, features illustrated or described as part of one embodiment can be used on another embodiment to yield a still further embodiment. Thus it is intended that the present application cover such modifications and variations as come within the scope of the appended claims and their equivalents. Other objects, features, and aspects of the present application are disclosed in, or are obvious from, the following detailed description. It is to be understood by one of ordinary skill in the art that the present discussion is a description of exemplary embodiments only, and is not to be construed as limiting the broader aspects of the present application.

Thus in accordance of this application there is provided compounds of formula (I), or stereoisomers thereof or pharmaceutically acceptable salts thereof:

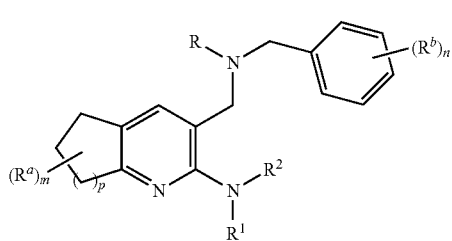

(I)

wherein,

R represents

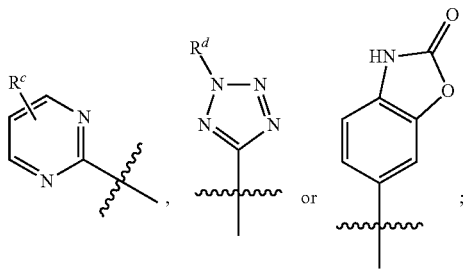

R¹ and R² are independently selected from hydrogen, acyl, haloalkyl, —(CHR$^e$)$_q$R³, an optionally substituted group selected from alkyl or cycloalkyl, wherein optional substituent, in each occurrence, is independently selected from halogen, cyano, hydroxyl, an alkyl, a haloalkyl or an alkoxy;

R³ is a group selected from alkoxy, haloalkoxy, cycloalkyl, aryl, heterocyclyl or heteroaryl, wherein R³ is optionally substituted with a group selected from halogen, cyano, hydroxyl, alkyl, haloalkyl or alkoxy;

R$^a$, in each occurrence, is independently selected from cyano, hydroxy, alkyl, haloalkyl or alkoxy;

R$^b$, in each occurrence, is independently selected from halogen, alkyl, haloalkyl, hydroxy, alkoxy or haloalkoxy;

R$^c$ is independently selected from hydrogen, cyano, halogen, —C(=O)—R$^f$, —CONR$^g$R$^h$, —C(=O)—CH=CH—NR$^i$R$^j$, an optionally substituted group selected from cycloalkyl, aryl, heteroaryl or heterocyclyl ring, wherein the optional substituent, in each occurrence, is selected independently from hydrogen, halogen, cyano, hydroxyl, alkyl, haloalkyl, alkoxy, alkoxyalkyl or haloalkoxy;

R$^d$ is selected from hydrogen or alkyl;

R$^e$, in each occurrence, is independently selected from hydrogen, alkyl or alkoxy;

R$^f$ is selected from hydrogen or alkyl;

R$^g$, R$^h$, R$^i$ and R$^j$ independently represents hydrogen or alkyl;

m is 0, 1 or 2;

n is 0, 1, 2 or 3;

p is 1 or 2; and q is 0, 1, 2, 3, 4 or 5.

In one embodiment, there is provided a compound of formula (Ia), or a stereoisomer thereof or a pharmaceutically acceptable salt thereof:

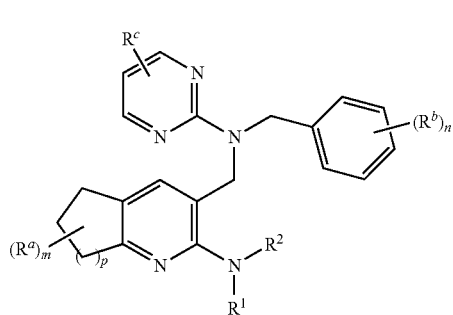

(Ia)

wherein,

R¹, R², R$^a$, R$^b$, R$^c$, p, m, n are as defined above.

In another embodiment, there is provided a compound of formula (Ib), or a stereoisomer thereof or a pharmaceutically acceptable salt thereof;

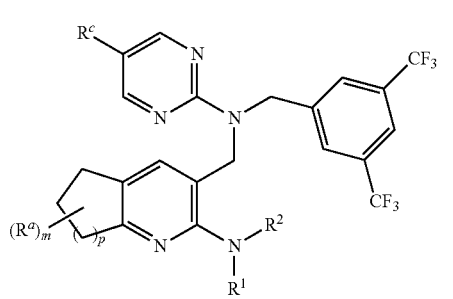

(Ib)

wherein,

R¹ and R² are independently selected from hydrogen or —(CHR$^e$)$_q$R³, wherein R³ represents cycloalkyl, aryl, heterocyclyl or heteroaryl;

R$^c$ represents optionally substituted ring selected from

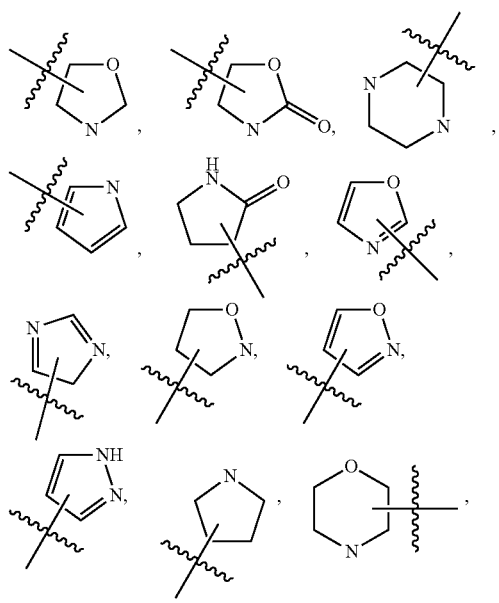

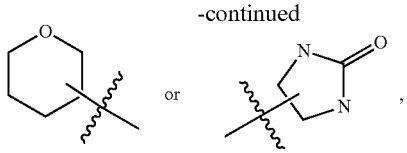

wherein the optional substituent is selected from halogen, cyano, hydroxyl, alkyl, haloalkyl, alkoxy, alkoxyalkyl or haloalkoxy;
q represents 1, 2 or 3; and
$R^a$, $R^e$ and p are as defined above.

In another embodiment, there is provided a compound of formula (Ic), or a stereoisomer thereof or a pharmaceutically acceptable salt thereof:

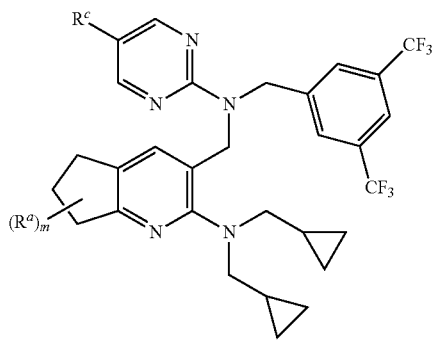

(Ic)

wherein,
$R^c$ represents

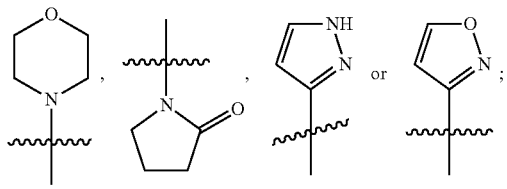

$R^a$ and m are as defined above.

In another embodiment, there is provided a compound of formula (Id), or a stereoisomer thereof or a pharmaceutically acceptable salt thereof:

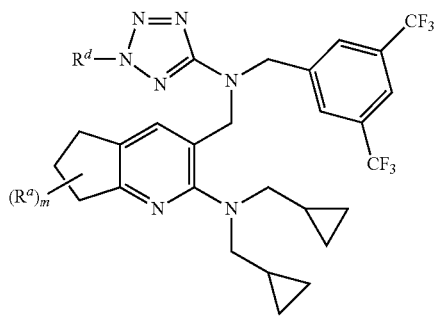

(Id)

wherein,
$R^d$, $R^a$ and m are as defined above.

In yet another embodiment there is provided a compound of formula (Ie), or a stereoisomer thereof or a pharmaceutically acceptable salt thereof:

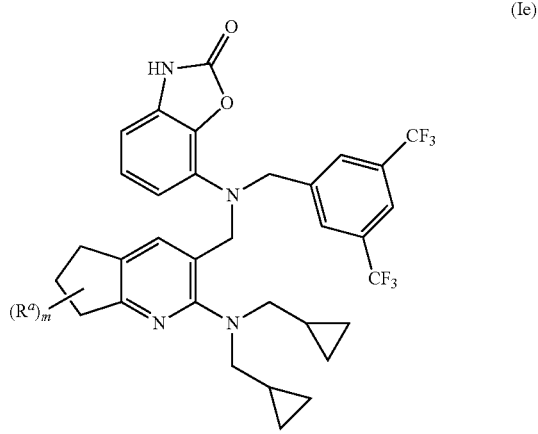

(Ie)

wherein,
$R^a$ and m are as defined in the above description of formula (I).

In another embodiment, specific compounds of formula (I) without any limitation are enumerated as follows:
3-(((3,5-bis(trifluoromethyl)benzyl)(5-bromopyrimidin-2-yl)amino)methyl)-N,N-bis(cyclopropylmethyl)-7,7-dimethyl-6,7-dihydro-5H-cyclopenta[b]pyridin-2-amine;
1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5-yl) pyrrolidin-2-one;
3-(((3,5-bis(trifluoromethyl)benzyl)(5-morpholinopyrimidin-2-yl)amino)methyl)-N,N-bis(cyclopropylmethyl)-7,7-dimethyl-6,7-dihydro-5H-cyclopenta[b]pyridin-2-amine;
1-(2-(((2-(bis(cyclopropylmethyl)amino)-7,7-dimethyl-6,7-dihydro-5H-cyclopenta[b]pyridine-3-yl)methyl)(3,5-bis(trifluoromethyl)benzyl)amino)pyrimidin-5-yl) ethanone;
(E)-1-(2-(((2-(bis(cyclopropylmethyl)amino)-7,7-dimethyl-6,7-dihydro-5H-cyclopenta[b]pyridine-3-yl)methyl)(3,5-bis(trifluoromethyl)benzyl)amino)pyrimidin-5-yl)-3-(dimethylamino)prop-2-en-1-one;
(E)-1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5-yl)-3-(dimethyl amino)prop-2-en-1-one;
3-(((3,5-bis(trifluoromethyl)benzyl)(5-(isoxazol-3-yl)pyrimidin-2-yl)amino)methyl)-N,N-bis(cyclopropylmethyl)-7,7-dimethyl-6,7-dihydro-5H-cyclopenta[b]pyridin-2-amine;
2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidine-5-carbonitrile;
2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidine-5-carboxamide;
3-(((3,5-bis(trifluoromethyl)benzyl)(5-morpholinopyrimidin-2-yl)amino)methyl)-N,N-bis(cyclopropylmethyl)-7-methyl-6,7-dihydro-5H-cyclopenta[b]pyridin-2-amine;
3-(((3,5-bis(trifluoromethyl)benzyl)(5-morpholinopyrimidin-2-yl)amino)methyl)-N,N-bis(cyclopropylmethyl)-8-methyl-5,6,7,8-tetrahydroquinolin-2-amine;

3-(((3,5-bis(trifluoromethyl)benzyl)(2H-tetrazol-5-yl)
amino)methyl)-N,N-bis(cyclopropylmethyl)-7,7-dimethyl-6,7-dihydro-5H-cyclopenta[b]pyridin-2-amine;
3-(((3,5-bis(trifluoromethyl)benzyl)(2-methyl-2H-tetrazol-5-yl)amino)methyl)-N,N-bis(cyclopropylmethyl)-7,7-dimethyl-6,7-dihydro-5H-cyclopenta[b]pyridin-2-amine;
3-(((3,5-bis(trifluoromethyl)benzyl)(2-isopropyl-2H-tetrazol-5-yl)amino)methyl)-N,N-bis(cyclopropylmethyl)-7,7-dimethyl-6,7-dihydro-5H-cyclopenta[b]pyridin-2-amine;
3-(((3,5-bis(trifluoromethyl)benzyl)(2-isobutyl-2H-tetrazol-5-yl)amino)methyl)-N,N-bis(cyclopropylmethyl)-7,7-dimethyl-6,7-dihydro-5H-cyclopenta[b]pyridin-2-amine;
3-(((3,5-bis(trifluoromethyl)benzyl)(2-methyl-2H-tetrazol-5-yl)amino)methyl)-N,N-bis(cyclo propylmethyl)-8,8-dimethyl-5,6,7,8-tetrahydroquinolin-2-amine;
6-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)benzo[d]oxazol-2(3H)-one;
3-(((3,5-bis(trifluoromethyl)benzyl)(2-methyl-2H-tetrazol-5-yl)amino)methyl)-N,N-bis(cyclopropylmethyl)-7-methyl-6,7-dihydro-5H-cyclopenta[b]pyridin-2-amine;
or stereoisomers thereof or pharmaceutically acceptable salts thereof.

The compounds of formula (I) may exist in the form of stereoisomers. Such stereoisomers are also a part of the present application.

The compounds of formula (I) may exist in the form of pharmaceutically acceptable salts. Such pharmaceutically acceptable salts are also a part of the present application.

In another embodiment, there is provided a pharmaceutical composition comprising a pharmaceutically acceptable carrier and a therapeutically effective amount of one or more compounds of formula (I) or a stereoisomer thereof or a pharmaceutically acceptable salt thereof.

One aspect of the above embodiment provides a pharmaceutical composition comprising one or more compounds selected from formula (Ia), (Ib), (Ic), (Id) or (Ie).

In another embodiment, there is provided compounds of formula (I) or stereoisomers thereof or pharmaceutically acceptable salt thereof, as CETP inhibitors.

In another embodiment, there is provided a method of administering CETP inhibitors in a subject (i.e., a patient), which comprises administering to said subject (i.e., a patient) a pharmaceutical composition comprising a therapeutically effective amount of a compound of formula (I) or a stereoisomer thereof or a pharmaceutically acceptable salt thereof. As used herein the term "subject" and "patient" can be the same and can be used interchangeably.

In another embodiment, there is provided a method of increasing the level of HDL cholesterol and/or a decreasing the level of very low density lipoprotein (VLDL) and low density lipoprotein (LDL) and/or increasing the ratio of HDL-C to LDL-C, which comprises administering to said subject a pharmaceutical composition comprising an effective amount of a compound of formula (I) or a stereoisomer thereof or a pharmaceutically acceptable salt thereof.

In another embodiment, there is provided a method for treating or reducing the risk of developing a disease or condition that may be treated or prevented by inhibition of CETP in a patient in need of such a treatment comprising the administration of a therapeutically effective amount of a compound of formula (I) or a stereoisomer thereof or a pharmaceutically acceptable salt thereof to said patient.

In another embodiment, there is provided a method of binding CETP in a patient in need of such a treatment comprising the administration of a therapeutically effective amount of the compound of formula (I), or a stereoisomer thereof or a pharmaceutically acceptable salt thereof to said patient.

In another embodiment, there is provided a method of increasing the level of HDL cholesterol in a patient in need of such a treatment comprising the administration of a therapeutically effective amount of the compound of formula (I), or a stereoisomer thereof or a pharmaceutically acceptable salt thereof to said patient.

In another embodiment, there is provided a method of lowering LDL cholesterol in a patient in need of such a treatment comprising the administration of a therapeutically effective amount of the compound of formula (I), or a stereoisomer thereof or a pharmaceutically acceptable salt thereof to said patient.

In another embodiment, there is provided a method of raising the ratio of increasing HDL cholesterol to LDL cholesterol in a patient in need of such a treatment comprising the administration of a therapeutically effective amount of the compound of the formula (I), or a stereoisomer thereof or a pharmaceutically acceptable salt thereof to said patient.

In another embodiment, there is provided a method of treating or preventing atherosclerosis in a patient in need of such a treatment comprising the administration of a therapeutically effective amount of the compound of formula (I), or a stereoisomer thereof or a pharmaceutically acceptable salt thereof to said patient.

The pharmaceutical composition of a compound of formula (I) may be administered enterally and/or parenterally. Parenteral administration includes subcutaneous, intramuscular, intradermal, intramammary, intravenous, and other administrative methods known in the art. Enteral administration includes solution, tablets, sustained release capsules, enteric coated capsules, syrups, beverages, foods, and other nutritional supplements. When administered, the present pharmaceutical compositions may be at or near body temperature. In some embodiments, the present pharmaceutical compositions may be below body temperatures. In other embodiments, the present pharmaceutical compositions may be above body temperatures.

The compounds of the present application may be administered in a wide variety of different dosage forms. For example, they may be combined with various pharmaceutically acceptable inert carriers in the form of, but not limited to, tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers may include solid diluents or fillers, sterile aqueous media, and various nontoxic organic solvents, etc. Moreover, oral pharmaceutical compositions may be sweetened and/or flavored. In general, the compounds of the present application may be present in such dosage forms at concentration levels ranging from about 0.1% to about 90% by weight.

In general, compounds of the present application for treatment may be administered to a subject in a suitable effective dose in the range of from about 0.01 to about 100 mg per kilogram of body weight of recipient per day, in some embodiments, in the range of from about 0.5 to about 50 mg per kilogram body weight of recipient per day, in still other embodiments, in the range of from about 0.1 to about 20 mg per kilogram body weight of recipient per day. The exemplary dose may be suitably administered once daily, or several sub-doses, e.g. 2 to 5 sub-doses, may be administered at appropriate intervals through the day, or on other appropriate schedules.

An embodiment of the present application provides the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present application claimed herein. All temperatures are in degrees Celsius (° C.) unless otherwise noted.

The following acronyms, abbreviations, terms and definitions have been used throughout the reaction scheme and experimental section.

DIBAL (Diisobutylaluminium hydride), CDCl₃ (Deuterated chloroform), CuI (Cuprous Iodide), CNBr (Cynogen bromide), DCM (Dichloromethane), DMF (N,N-dimethylformamide), DMF-DMA (N,N-dimethylformamide dimethyl acetal), DMSO (Dimethyl sulfoxide), HCl (hydrochloric acid), H₂O₂ (Hydrogen peroxide), AcOH (Acetic acid), MeOH (Methanol), NaOMe (Sodium methoxide), LDA (Lithium Diisopropylamide), LAH (Lithium aluminium hydride), NH₂NH₂.H₂O (Hydrazine hydrate), NH₂OH.HCl (hydroxylamine hydrochloride), K₂CO₃ (Potassium Carbonate), KOH (Potassium hydroxide), KCN (Potassium cyanide), Pd (Palladium), Pd(OAc)₂ (Palladium (II) acetate), Pd₂(dba)₃ (Tris(dibenzylideneacetone)dipalladium(0)), CNBr (Cyanogen bromide), POCl₃ (Phosphorus oxychloride), PCl₅ (Phosphorus pentachloride), PdCl₂ (Palladium (II) chloride), Pd(PPh₃)₄ (Tetrakis(triphenylphosphine)palladium(0)), NaCN (Sodium cyanide), Na₂CO₃ (Sodium Carbonate), NaOH (Sodium hydroxide), NaCl (Sodium chloride), Na(CN)BH₃ (Sodium cyanoborohydride), Na₂SO₄ (Sodium Sulfate), NaOBuᵗ (sodium t-butoxide), NaBH₄ (Sodium borohydride), Na(OAc)₃BH (Sodium triacetoxyborohydride), NaN₃ (Sodium azide), SnCl₂ (Tin (II) chloride), Ti(i-Pro)₄ (Titanium(IV)isopropoxide), SOCl₂ (Thionyl chloride), H₂O (Water), ZnBr₂ (Zinc bromide), Zn(CN)₂ (Zinc cyanide), H₂ (Hydrogen gas), H₂SO₄ (Sulfuric acid), EDTA (Ethylenediaminetetraacetic acid).

Another embodiment of the present application provides a process for the preparation of compounds of formulae (10) & (11), both of which represent respectively a sub-group of a compound of formula (I), wherein all symbols/variables are as defined earlier unless otherwise stated. The process is represented by Scheme-1.

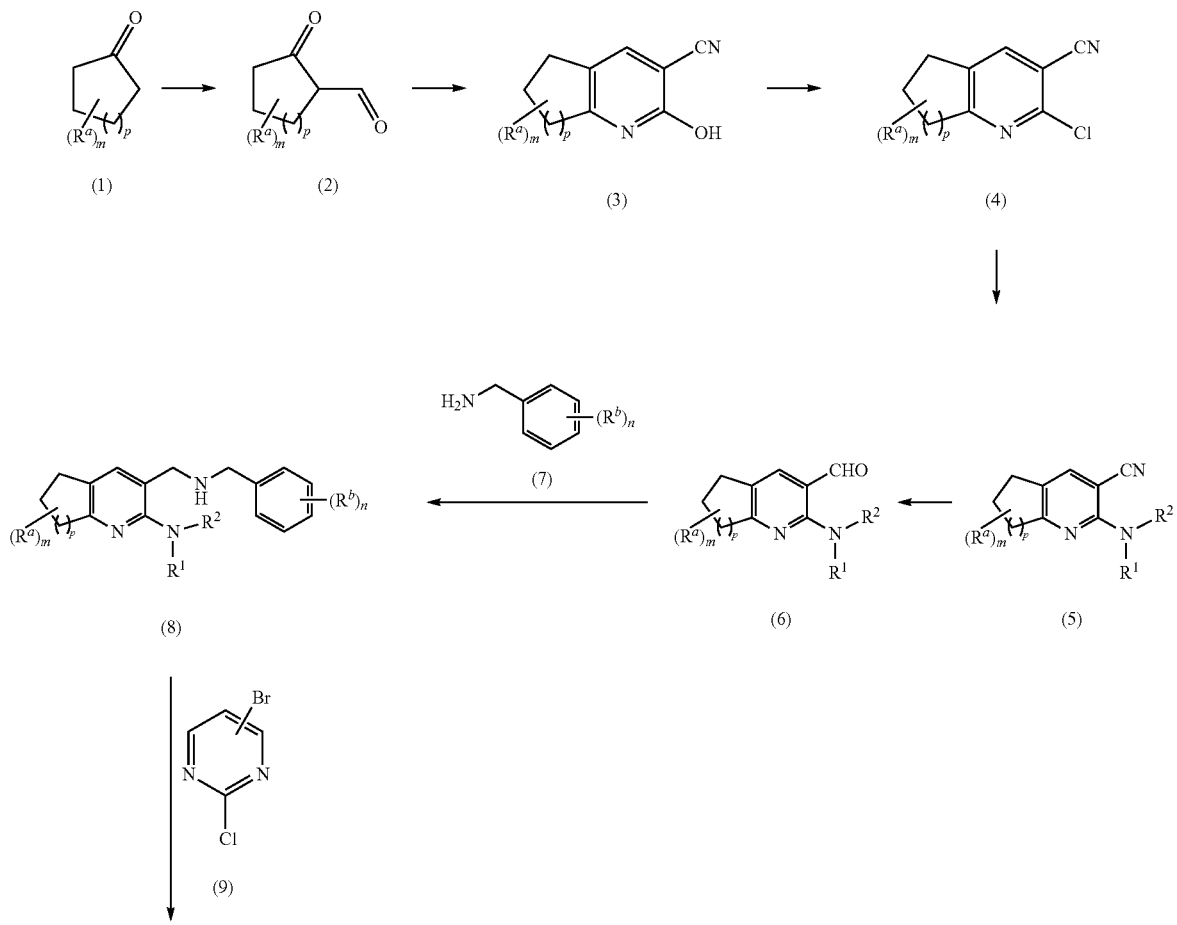

-continued

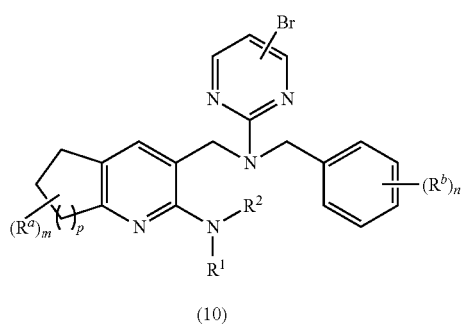

(10)

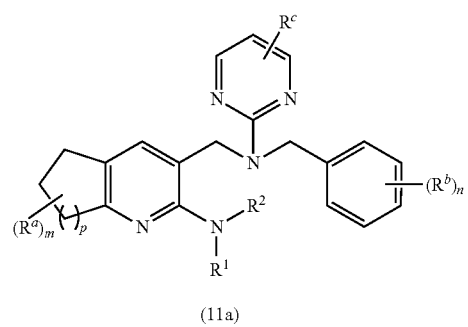

(11a)

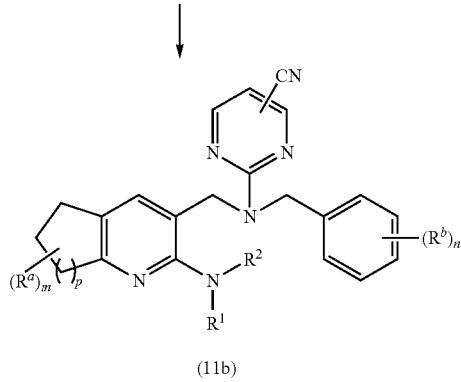

(11b)

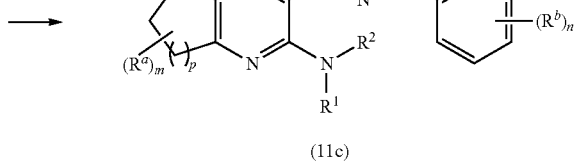

(11c)

Optionally substituted cycloalkanone of formula (1), wherein $R^a$, m and p are as defined in the description of formula (I), is reacted with a formate ester, such as ethyl formate in the presence of sodium metal, NaOMe, and the like to obtain an optionally substituted 2-oxocyclolkanone carbaldehyde of formula (2). The compound (2) can be further condensed with cyanoacetamide in the presence of a base, such as piperidine-acetate to obtain a compound of formula (3).

Amino substitutions on the ring of the compound of formula (5) can be obtained by first converting compound of formula (3) to compound of formula (4) using suitable reagents, such as $SOCl_2$, $PCl_5$ and the like; followed by using common nucleophilic substitution reactions known in the art to obtain a compound of formula (5).

A compound of formula (6) can be obtained by reduction of the cyano group of compound (5) to aldehyde using reagents, such as DIBAL, $SnCl_2$—HCl, Lithium N,N'-dimethyl ethylenediaminoaluminium hydride, or by reduction of nitrile in presence of $H_2$-Raney Nickle or LAH or sodium borohydride and the like, followed by in-situ hydrolysis of the intermediate imine A compound of formula (8) can be obtained by condensing a compound of formula (6) with an optionally substituted benzylamine of formula (7) in the presence of a suitable reagent such as sodium cyanoborohydride, sodium triacetoxyborohydride, Ti(i-PrO)$_4$ and NaBH$_4$, pyridine-borane complex and the like in a suitable solvent. $R^a$, $R^b$, m, n and p are as defined in the description of formula (I).

A compound of formula (10) can be obtained by reacting the secondary amino group of compound of formula (8) with a 2-chloro-bromopyrimidine of formula (9), in the presence of a base such as potassium carbonate, sodium carbonate, potassium acetate, cesium carbonate and the like, in a solvent such as such as anhydrous DMF, 1,4-dioxane, DMSO, acetonitrile and the like.

Compound of formula (11a), wherein $R^c$ represents an optionally substituted group selected from cycloalkyl, aryl, heteroaryl or heterocyclyl ring as defined in formula (I), can be obtained by nucleophilic substitutions on the pyrimidine ring of formula (10), by using a base such as potassium carbonate, sodium carbonate, potassium acetate, cesium carbonate, sodium t-butoxide and the like, in the presence of a solvent such as anhydrous toluene, DMF, 1,4-dioxane, DMSO, acetonitrile and the like. Some compounds of formula (I) can be prepared by using palladium catalysts like Pd(OAc)$_2$, Pd$_2$(dba)$_3$, PdCl$_2$ in the presence of a ligand selected from biphenyl di-t-butylphosphine, triphenylphosphine, 2-(dicyclohexylphosphino)biphenyl, xanthphos and the like. For example a compound of formula (11b) can be obtained by palladium catalysed cyanation of compound of formula (8) using Zn(CN)$_2$, KCN and the like. Some compounds of the formula (I) can be prepared through CuI mediated Buchwald Coupling in the presence of a variety of ligands used for such purposes, which include for example trans-1,2-diaminocyclohexane, quinolin-8-ol, bis-(2-aminoethyl)amine, and the like.

Further a compound of formula (11c) can be obtained by hydrolyzing the nitrile group in compound of formula (11b) using methods known in the art such as acid catalyzed hydrolysis in the presence of HCl, $H_2SO_4$ and other inorganic acids or base catalyzed hydrolysis in the presence of $H_2O_2$ and $K_2CO_3$ or KOH.

In another embodiment there is provided a process for the preparation of a compound of formulae (13), (14), (15) & (16), all of which represent respectively a sub-group of a compound of formula (I), wherein all symbols/variables are as defined earlier unless otherwise stated. The process is represented by Scheme-2.

Scheme 2:

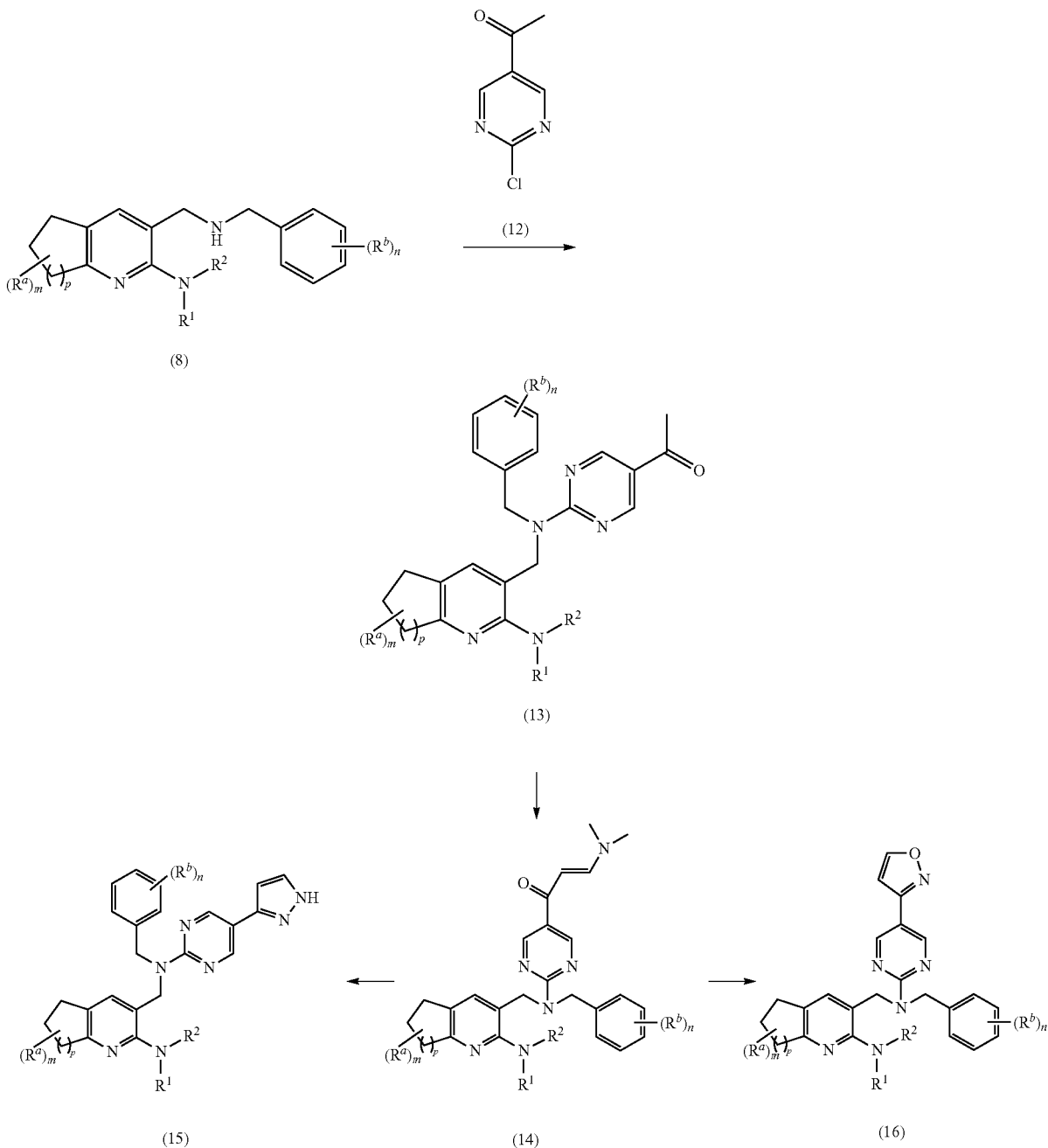

A compound of formula (13) can be obtained by reacting the secondary amino group of compound of formula (8) with a compound of formula (12), in the presence of a base such as potassium carbonate, sodium carbonate, potassium acetate, cesium carbonate, and the like, in a solvent such as anhydrous DMF, 1,4-dioxane, DMSO, acetonitrile, and the like.

A compound of formula (13) can be converted to a compound of formula (14) in the presence of an appropriate reagent such as N,N-dimethylformamide dimethylacetal, in the presence of a solvent such as toluene, DCM, 1,2-dichloroethane, 1,4-dioxane, and the like.

A compound of formula (14) can be converted to a compound of formula (15) in the presence of an appropriate reagent such as $NH_2NH_2 \cdot H_2O$, in the presence of a solvent such as ethanol, methanol, isopropanol, n-butanol, and the like.

A compound of formula (14) can be converted to a compound of formula (16) in the presence of an appropriate reagent such as $NH_2OH \cdot HCl$, in the presence of a solvent such as ethanol, methanol, isopropyl alcohol, n-butanol, and the like.

In another embodiment there is provided a process for the preparation of compounds of formulae (17), (18) &(19), all of which represent respectively a sub-group of a compound of formula (I), wherein all symbols/variables are as defined earlier unless otherwise stated. The process is represented by Scheme-3:

Scheme 3:

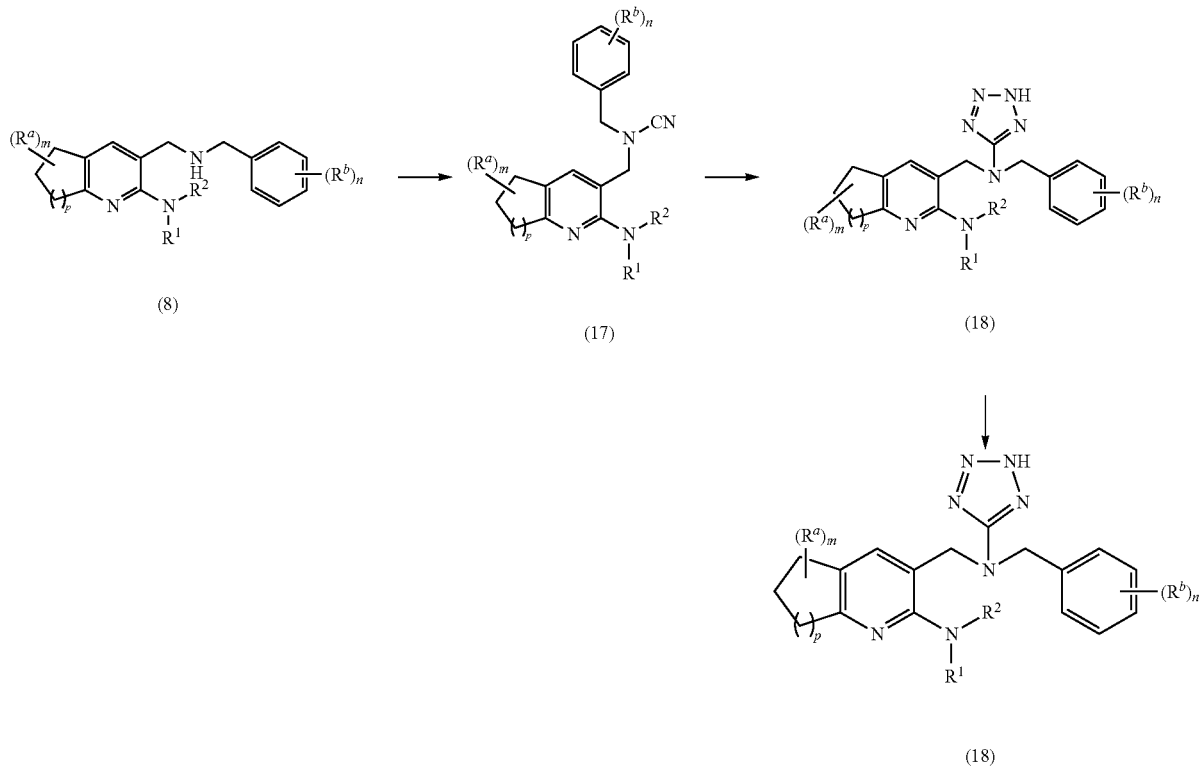

A compound of formula (8) is converted to a compound of formula (17) in the presence of a reagent, such as CNBr, NaCN, and the like, in a suitable solvent such as dimethylformamide, acetonitrile, a ($C_1$-$C_{10}$) alcohol, or the like, along with a base such as sodium bicarbonate, sodium carbonate, potassium carbonate, cesium carbonate, potassium bicarbonate, and the like. The temperature of the reaction is generally maintained from about 25° C. to about 55° C., and the duration of the reaction typically can range from about 20 minutes to about 5 hours.

A compound of formula (17) is converted to a compound of formula (18) by reacting with sodium azide or potassium azide, in the presence of a zinc salt such as $ZnBr_2$. Suitable solvent for this reaction can be selected from N,N-dimethylformamide, acetonitrile, ($C_1$-$C_{10}$) alcohols, and the like.

A compound of formula (18) can be converted into a compound of formula (19) by reacting with an alkylating reagent such as alkyl halide or dialkyl sulphate, in the presence of a base such as sodium hydroxide, potassium hydroxide, potassium carbonate, sodium hydride, potassium hydride, and the like, along with a phase-transfer catalyst such as tetraalkylammoniumhalide or tetraarylammoiumhalide, in a solvent medium such as water, dimethylformamide, acetonitrile, and the like.

In another embodiment there is provided a process for the preparation of a compound of formula (20), which represents a sub-group of a compound of formula (I), wherein all symbols/variables are as defined earlier unless otherwise stated. The process is represented by Scheme-4.

Scheme 4:

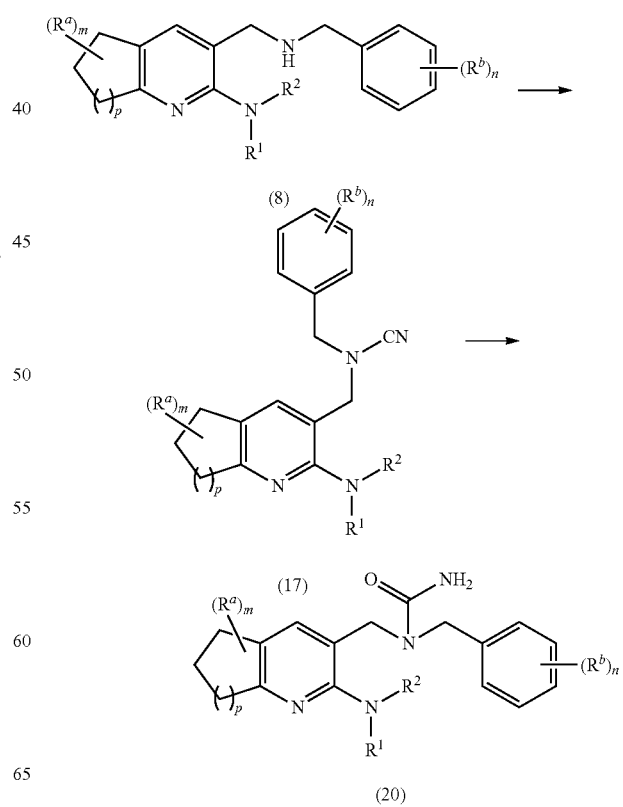

A compound of formula (8) can be converted to a compound of formula (17) by a procedure as defined above.

A compound of formula (17) can be hydrolyzed in the presence of a base such as KOH, NaOH, and the like, along with a catalytic amount of $H_2O_2$, typically at a temperature in the range from about 25 to about 100° C. for a period of time from about 30 minutes to about 6 hours, to yield a compound of formula (20).

In another embodiment there is provided a process for the preparation of a compound of formula (24), which represents a sub-group of a compound of formula (I), wherein all symbols/variables are as defined earlier unless otherwise stated. The process is represented by Scheme-5.

A compound of formula (22) can be reacted with a compound of formula (23) wherein $X^1$ is a leaving group such as halogen, mesyloxy, tosyl, and the like, to obtain a compound of formula (24), in the presence of a base like sodium hydride or potassium hydride. The reaction can be carried in a solvent such as N,N-dimethylformamide, acetonitrile, tetrahydrofuran, toluene, and the like. The temperature of the reaction may be maintained from about 25° C. to about 55° C., and the duration of the reaction typically can range from about 20 minutes to about 5 hours.

As used in the examples and preparations that follow, the terms used therein shall have the meanings indicated: "g" refers to grams, "mg" refers to milligrams, "μg" refers to Scheme 5:

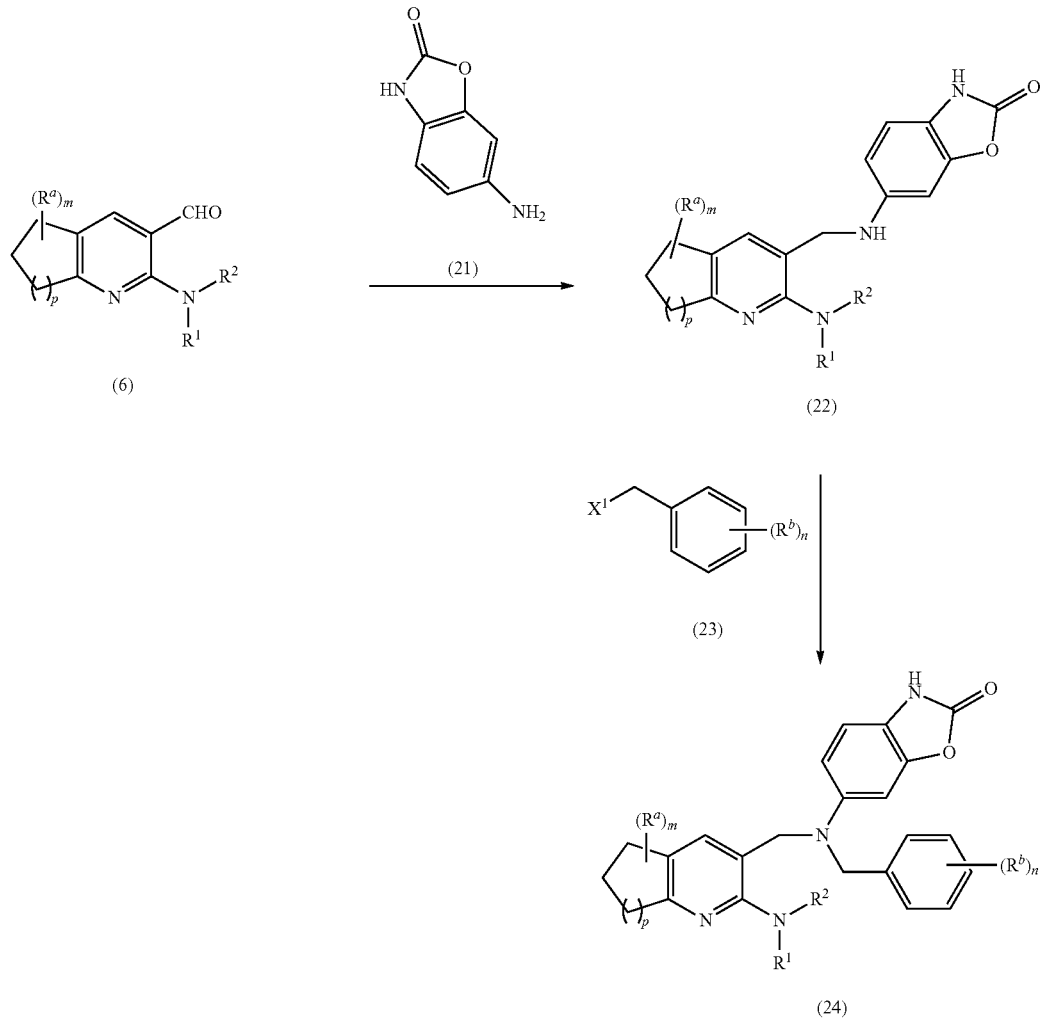

Reductive amination of a compound of formula (6) with a compound of formula (21) can be carried out in the presence of a reducing agent, such as $Na(CN)BH_3$, $Na(OAc)_3BH$, $NaBH_4$ and the like, in ($C_1$-$C_{10}$) alcohol solvent medium such as ethanol, propanol, isopropanol, and the like, along with an acid, such as acetic acid or diluted hydrochloric acid, could yield a compound of formula (22). The temperature of the reaction may be maintained from about 25° C. to about 35° C., and the duration of the reaction typically can range from about 30 minutes to about 5 hours.

micrograms, "mol" refers to moles, "mmol" refers to millimoles, "L" refers to liters, "mL" or "ml" refers to milliliters, "μL" refers to microliters, "nm" refers to nanometers, "conc." refers to concentrated, "M" refers to molar, "mM" refers to millimolar, "μM" refers to micromolar, "nm" or "nM" refers to nanomolar, "TLC" refers to thin layer chromatography, "HPLC" refers to high performance liquid chromatography, "min" refers to minute or minutes, "h" or "hr" refers to hour or hours; "s" refers to singlet, "d" refers to doublet, "t" refers to triplet, "q" refers to quartet, "m" refers to multiplet, "dd" refers to "doublet of doublets", "br" refers to broad, "LC" refers to liquid chromatograph, "MS" refers to mass spectroscopy, "ESI" refers to electrospray ionization, "CI" refers to chemical ionization, "M" refers to molecular ion, "NMR" refers to nuclear magnetic resonance spectroscopy, "MHz" refers to megahertz.

EXAMPLES

Example 1

Synthesis of 3-(((3,5-bis(trifluoromethyl)benzyl)(5-bromopyrimidin-2-yl)amino)methyl)-N,N-bis(cyclopropylmethyl)-7,7-dimethyl-6,7-dihydro-5H-cyclopenta[b]pyridin-2-amine

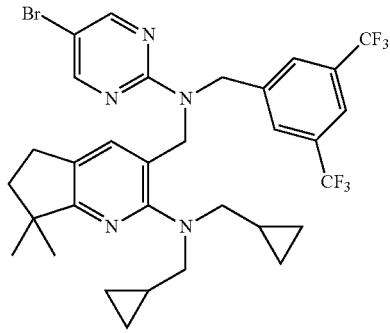 [SMILES: CC1(C)CCc2cc(CN(Cc3cc(C(F)(F)F)cc(C(F)(F)F)c3)c3ncc(Br)cn3)c(N(CC3CC3)CC3CC3)nc21]

Step-1: Synthesis of 2,2-dimethylcyclopentanone

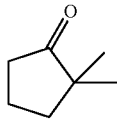

A solution of cyclopentanone (5 g, 59 mmol) in toluene (50 mL) was added to a suspension of sodium t-pentoxide (13 g, 118 mmol) in toluene (20 mL). Dimethyl sulfate (14.8 g, 118 mmol) was added drop wise to the mixture thus obtained at a temperature of 5° C. The mixture was warmed to a temperature of about 20-35° C. and was stirred for about 28 h. The reaction mixture was treated with saturated sodium bisulfite (NaHSO$_3$) solution and was extracted with ethyl acetate (3×100 mL). The combined organic layer was washed with brine, dried over sodium sulfate and concentrated under reduced pressure to obtain the desired product as a brown liquid (5.2 g). MS (ESI): 111 (M−1)$^+$.

Step-2: Synthesis of 2-hydroxy-7,7-dimethyl-6,7-dihydro-5H-cyclopenta[b]pyridine-3-carbonitrile

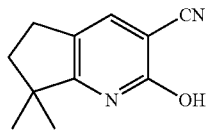

Sodium metal (0.854 g, 0.8 mol) was added portion wise to diethyl ether (20 mL) with continuous stirring until a clear suspension was formed. To this suspension, 2,2-dimethylcyclopentanone (5.2 g, 46.4 mmol), ethyl formate (4.1 g, 55.7 mmol) were added drop wise and the reaction mixture was stirred at a temperature of about 20-35° C. for about 28 h. The mixture was treated with methanol and filtered. The filtrate was concentrated under reduced pressure and the residue, 3,3-dimethyl-2-oxocyclopentanecarbaldehyde sodium salt, was directly used in the next step.

To a solution of 3,3-dimethyl-2-oxocyclopentanecarbaldehyde sodium salt (5 g, 30.9 mmol) in water (10 mL) was added cyanoacetamide (2.5 g, 30.9 mmol), piperidine (2.6 g, 30.9 mmol in 10 mL water) and acetic acid (1 mL) in that order. The reaction mixture was stirred at 100° C. for about 26 h and then cooled to a temperature of about 20-35° C. The reaction mass was adjusted to pH value of about 6 and was then filtered off to obtain a crude product. The crude product was purified by column chromatography (60-120 mesh silica gel) with 10% ethyl acetate in petroleum ether as the eluent to obtain the desired product as a brown liquid (0.8 g).

$^1$H NMR (400 MHz, CDCl$_3$): δ 13.6 (bs, 1H), 7.75 (s, 1H), 2.73 (t, J=8.0 Hz, 2H), 2.02 (t, J=8.0 Hz, 2H), 1.40 (s, 6H). MS (ESI): 189 (M+1)$^+$.

Step-3: Synthesis of 2-(bis(cyclopropylmethyl)amino)-7,7-dimethyl-6,7-dihydro-5H-cyclopenta[b]pyridine-3-carbonitrile

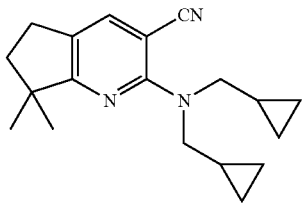 [SMILES: CC1(C)CCc2cc(C#N)c(N(CC3CC3)CC3CC3)nc21]

Phosphorous oxychloride (1.9 mL, 24 mmol) was added to 2-hydroxy-7,7-dimethyl-6,7-dihydro-5H-cyclopenta[b]pyridine-3-carbonitrile (0.8 g, 4.3 mmol), obtained in step-1, at 0° C. over a period of about 10 min. The mixture was warmed to a temperature of about 20-35° C. and was heated further to about 80° C. The mixture was stirred at about 80° C. for about 18 h. The reaction mixture was cooled to a temperature of about 20-35° C. and then was poured into crushed ice. The solid which separated out was filtered off and dried under reduced pressure to get 2-chloro-7,7-dimethyl-6,7-dihydro-5H-cyclopenta[b]pyridine-3-carbonitrile (0.7 g).

$^1$H NMR (400 MHz, CDCl$_3$): δ 7.74 (s, 1H), 2.89 (t, J=7.2 Hz, 2H), 2.05 (t, J=7.6 Hz, 2H), 1.30 (s, 6H). MS (ESI): 207 (M+1)$^+$.

2-Chloro-7,7-dimethyl-6,7-dihydro-5H-cyclopenta[b]pyridine-3-carbonitrile (0.7 g, 3.4 mmol) obtained in the previous step, and bis(cyclopropylmethyl)amine were heated with stirring at 100° C. for about 20 h. The reaction mixture was cooled to a temperature of about 20-35° C. and was purified by column chromatography (60-120 mesh silica gel) using about 10% ethyl acetate in petroleum ether as eluent to obtain the desired product as a pale yellow liquid (0.7 g).

$^1$H NMR (400 MHz, CDCl$_3$): δ 7.48 (s, 1H), 3.63 (d, J=7.2 Hz, 2H), 1.92 (t, J=6.8 Hz, 2H), 1.20 (s, 6H), 0.54-0.48 (m, 4H), 0.30-0.27 (m, 4H). MS (ESI): 296 (M+1)$^+$.

Step-4: Synthesis of 2-(bis(cyclopropylmethyl)amino)-7,7-dimethyl-6,7-dihydro-5H-cyclopenta[b]pyridine-3-carbaldehyde

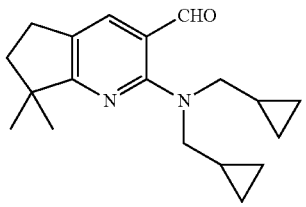 [SMILES: CC1(C)CCc2cc(C=O)c(N(CC3CC3)CC3CC3)nc21]

2-(bis(cyclopropylmethyl)amino)-7,7-dimethyl-6,7-dihydro-5H-cyclopenta[b]pyridine-3-carbonitrile (2.1 g, 7.2 mmol), obtained in step-3, was dissolved in dry dichloromethane (10 mL) was added drop wise to 1M solution of DIBAL in toluene (4.2 mL, 14 mmol) at about −78° C. The reaction mixture was stirred at the same temperature for about 2 h. The reaction mixture was warmed to 0° C., and was adjusted to a pH value of about 6 with diluted HCl. The aqueous mass was extracted with ethyl acetate (3×200 mL). The combined organic layer was washed with brine, dried over sodium sulfate and concentrated under reduced pressure.

The crude product was purified by column chromatography using silica gel (60-120 mesh) and about 5% ethyl acetate in dichloromethane as eluent to obtain the product as a pale yellow liquid (1 g).

$^1$H NMR (400 MHz, CDCl$_3$): δ 10.11 (s, 1H), 7.79 (s, 1H), 3.38 (d, J=6.8 Hz, 4H), 2.78 (t, J=7.6 Hz, 2H), 1.95 (t, J=7.2 Hz, 2H), 1.24 (s, 6H), 1.20-1.08 (m, 2H), 0.50-0.40 (m, 4H), 0.17-0.13 (m, 4H). MS (ESI): 299 (M+1)$^+$.

Step-5: Synthesis of 3-((3,5-bis(trifluoromethyl)benzylamino)methyl)-N,N-bis(cyclopropylmethyl)-7,7-dimethyl-6,7-dihydro-5H-cyclopenta[b]pyridin-2-amine

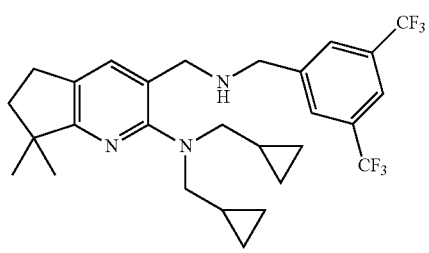 [SMILES: CC1(C)CCc2cc(CNCc3cc(C(F)(F)F)cc(C(F)(F)F)c3)c(N(CC3CC3)CC3CC3)nc21]

To a solution of 2-(bis(cyclopropylmethyl)amino)-7,7-dimethyl-6,7-dihydro-5H-cyclopenta[b]pyridine-3-carbaldehyde (1.2 g, 4 mmol), obtained in step-4, and bis(trifluoromethyl)benzylamine (7.1 g, 29.4 mmol) in methanol (10 mL), was added glacial acetic acid (0.3 mL) and the resulting mixture was stirred for about 15 min at a temperature of about 20-35° C. Sodium cyanoborohydride (0.257 g, 4 mmol) was added portion wise to this reaction mixture and the reaction mixture was stirred for about 3 h.

After concentrating the mixture under reduced pressure, it was extracted with water (30 mL) and dichloromethane (2×30 mL). The organic layer was collected, washed with brine, dried over sodium sulfate and concentrated under reduced pressure to get the crude product. The crude product was purified by column chromatography using silica gel (60-120 mesh) and eluted with 50% petroleum ether in ethyl acetate to obtain the pure product as a pale yellow liquid (0.7 g).

$^1$H NMR (400 MHz, CDCl$_3$): δ 7.83 (s, 2H), 7.75 (s, 2H), 7.30 (s, 1H), 3.87 (s, 2H), 3.80 (s, 2H), 2.98 (d, J=7.2 Hz, 4H), 2.79 (t, J=6.8 Hz, 2H), 1.95 (t, J=7.6 Hz, 2H), 0.84-0.78 (m, 2H), 0.31-0.28 (m, 4H), −0.01 (m, 4H). MS (ESI): 526 (M+1)$^+$.

Step-6: Synthesis of 3-(((3,5-bis(trifluoromethyl)benzyl)(5-bromopyrimidin-2-yl)amino)methyl)-N,N-bis(cyclopropylmethyl)-7,7-dimethyl-6,7-dihydro-5H-cyclopenta[b]pyridin-2-amine

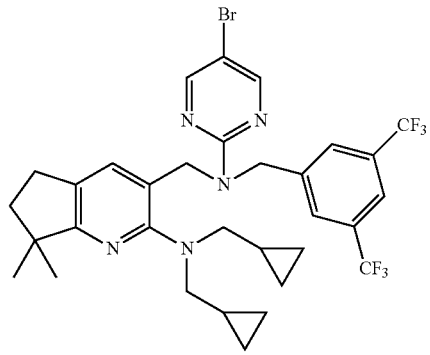 [SMILES: CC1(C)CCc2cc(CN(Cc3cc(C(F)(F)F)cc(C(F)(F)F)c3)c3ncc(Br)cn3)c(N(CC3CC3)CC3CC3)nc21]

To a mixture of 3-(((3,5-bis(trifluoromethyl)benzyl)(4-bromophenyl)amino)methyl)-N,N-bis(cyclopropylmethyl)-7,7-dimethyl-6,7-dihydro-5H-cyclopenta[b]pyridin-2-amine (1.0 g, 1.9 mmol), obtained in step-5, and 2-chloro-5-bromopyrimidine (0.735 g, 3.8 mmol) in anhydrous dimethylformamide, potassium carbonate (0.525 g, 3.8 mmol) was added. The reaction mixture was heated with stirring at 100° C. for about 18 h. Thereafter, the reaction mixture was allowed to cool to a temperature of about 20-35° C. The mixture was then diluted with water (20 mL) and extracted with ethyl acetate (3×50 mL). The combined organic layer was washed with brine, dried over sodium sulfate and concentrated under reduced pressure to get the crude product. The crude product was purified by chromatography using silica gel (100-200 mesh) and about 10% ethyl acetate in petroleum ether as eluent to obtain the pure product as a brown viscous liquid (0.3 g).

$^1$H NMR (400 MHz, CDCl$_3$): δ 8.69 (s, 3H), 8.35 (s, 2H), 7.70-7.66 (m, 2H), 7.17 (s, 1H), 4.99 (s, 2H), 4.79 (s, 2H), 2.69 (t, J=6.8 Hz, 2H), 1.21 (s, 6H), 0.97-0.81 (m, 2H), 0.30-0.26 (m, 4H), −0.00 (m, 4H). MS (ESI): 684 (M+2)$^+$, 682 (M+1)$^+$.

Example 2

Synthesis of 1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5-yl) pyrrolidin-2-one

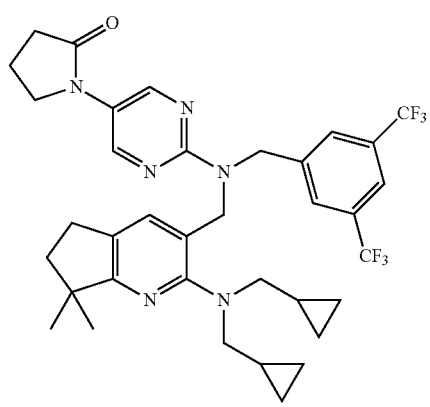 [SMILES: CC1(C)CCc2cc(CN(Cc3cc(C(F)(F)F)cc(C(F)(F)F)c3)c3ncc(N4CCCC4=O)cn3)c(N(CC3CC3)CC3CC3)nc21]

To a mixture of 3-(((3,5-bis(trifluoromethyl)benzyl)(4-bromophenyl)amino)methyl)-N,N-bis(cyclopropylmethyl)-7,7-dimethyl-6,7-dihydro-5H-cyclopenta[b]pyridin-2-amine, obtained in step-6 of Example 1, (0.15 g, 0.2 mmol), oxazolidin-2-one (0.037 g, 0.4 mmol) and anhydrous 1,4-dioxane (10 mL) was added potassium carbonate (0.06 g, 0.4 mmol), CuI (0.008 g, 0.04 mmol) and trans-1,2-diaminocyclohexane (0.07 g, 0.06 mmol) sequentially. The reaction mixture was degassed for about 10 min with argon and heated at 100° C. with stirring for about 70 h.

The reaction mixture was cooled to a temperature of about 20-35° C., filtered off through celite. The filtrate was concentrated under reduced pressure to get the crude product which was purified by column chromatography using silica gel (100-200 mesh) and about 10% ethyl acetate in petroleum ether as eluent to yield the desired product as a white solid (0.02 g, 13%).

$^1$H NMR (400 MHz, CDCl$_3$): δ 8.61 (s, 2H), 7.71 (s, 3H), 7.20 (s, 1H), 5.02 (s, 2H), 4.82 (s, 2H), 3.82 (t, J=6.8 Hz, 2H), 2.96 (d, J=6.8 Hz, 4H), 2.69 (t, J=7.2 Hz, 2H), 2.61 (t, J=8.0 Hz, 2H), 2.26-2.18 (m, 2H), 1.91 (t, J=7.2 Hz, 2H), 1.21 (s, 6H), 0.88-0.70 (m, 2H), 0.29-0.27 (m, 4H). MS (ESI): 681 (M+1)$^+$

Example 3

Synthesis of 3-(((3,5-bis(trifluoromethyl)benzyl)(5-morpholinopyrimidin-2-yl)amino)methyl)-N,N-bis(cyclopropylmethyl)-7,7-dimethyl-6,7-dihydro-5H-cyclopenta[b]pyridin-2-amine

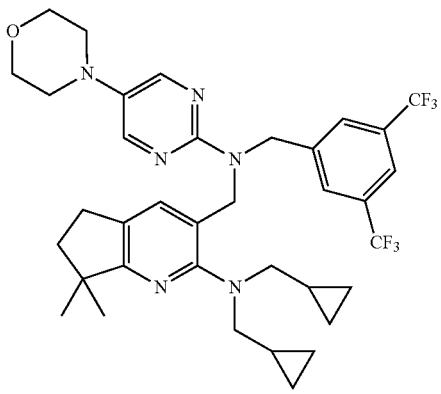 [SMILES: CC1(C)CCc2cc(CN(Cc3cc(C(F)(F)F)cc(C(F)(F)F)c3)c3ncc(N4CCOCC4)cn3)c(N(CC3CC3)CC3CC3)nc21]

A mixture of 3-(((3,5-bis(trifluoromethyl)benzyl)(4-bromophenyl)amino)methyl)-N,N-bis(cyclopropylmethyl)-7,7-dimethyl-6,7-dihydro-5H-cyclopenta[b]pyridin-2-amine, obtained in step-6 of example-1, (0.500 g, 0.7 mmol), morpholine (0.013 g, 2 mmol) and Pd$_2$(dba)$_3$ (0.114 g, 0.2 mmol), biphenyl di-t-butylphosphine (0.025 g, 0.08 mmol) and sodium t-butoxide (0.105 g, 1.05 mmol) in toluene (10 mL) was heated with stirring at 100° C. for about 2 h under argon atmosphere.

The reaction mixture was cooled to a temperature of 20-35° C., water (10 mL) was added to it and the aqueous mass thus obtained was then extracted with ethyl acetate (3×15 mL). The combined organic layer was dried over sodium sulfate and concentrated under reduced pressure to get the crude product. The crude product was purified by column chromatography using silica gel (100-200 mesh) and about 10% ethyl acetate in petroleum ether as eluent to yield the desired product as a white solid (0.120 g).

$^1$H NMR (400 MHz, DMSO-d$_6$): δ 8.14 (s, 2H), 7.70 (s, 3H), 7.19 (s, 1H), 4.98 (s, 2H), 4.79 (s, 2H), 3.87 (d, J=9.6 Hz, 4H), 3.06-3.04 (m, 4H), 2.96-2.94 (m, 4H), 2.68 (t, J=6.8 Hz, 2H), 1.90 (t, J=6.8 Hz, 2H), 1.21 (s, 6H), 0.80-0.78 (m, 2H), 0.30-0.28 (m, 4H), −0.013 (m, 4H). MS (ESI): 689 (M+1)$^+$

Example 4

Synthesis of 1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5-yl)ethanone

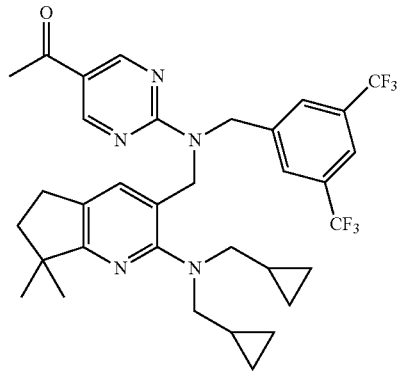 [SMILES: CC(=O)c1cnc(N(Cc2cc(C(F)(F)F)cc(C(F)(F)F)c2)Cc2cc3c(nc2N(CC2CC2)CC2CC2)C(C)(C)CC3)nc1]

To 3-(((3,5-bis(trifluoromethyl)benzylamino)methyl)-N,N-bis(cyclopropylmethyl)-7,7-dimethyl-6,7-dihydro-5H-cyclopenta[b]pyridin-2-amine, obtained in step-5 of example 1, (0.5 g, 0.9 mmol) in DMF (10 mL) were added 1-(2-chloropyrimidin-5-yl)ethanone (0.14 g, 0.0009 mmol), potassium carbonate (0.39 g, 2.7 mmol). The reaction mixture was heated with stirring at about 70° C. for about 2 h. The reaction mixture was cooled to a temperature of about 20-35° C., diluted with water (20 mL) and the aqueous mass was then extracted with ethyl acetate (3×40 mL). The combined organic layer was dried over sodium sulfate and then concentrated under reduced pressure to obtain the crude product. The title compound was then isolated by preparative TLC using dichloromethane (0.36 g) as an eluent.

$^1$H NMR (400 MHz, DMSO-d$_6$): δ 8.93-8.91 (m, 3H), 7.75 (s, 3H), 5.10 (s, 2H), 4.9 (s, 2H), 2.97 (d, J=6.6 Hz, 4H), 2.71-2.67 (m, 2H), 2.52 (s, 3H), 1.96-1.94 (m, 2H), 0.89-0.81 (m, 2H), 0.32-0.28 (m, 4H), 0.07 (s, 6H), 0.04-0.01 (m, 4H). MS (ESI): 646 (M+1)$^+$.

Example 5

Synthesis (E)-1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5-yl)-3-(dimethyl amino)prop-2-en-1-one

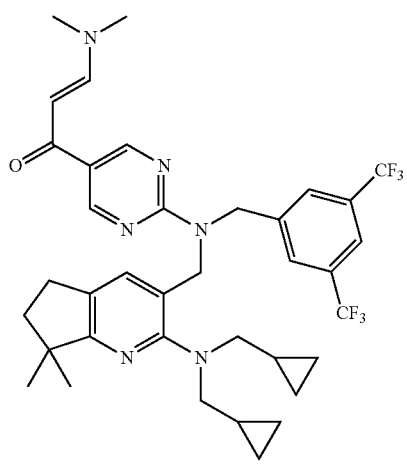 [SMILES: CN(C)/C=C/C(=O)c1cnc(N(Cc2cc(C(F)(F)F)cc(C(F)(F)F)c2)Cc2cc3c(nc2N(CC2CC2)CC2CC2)C(C)(C)CC3)nc1]

1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5-yl)ethanone (0.40 g, 0.6 mmol), obtained in Example 4, and N,N-dimethylformamide dimethyl acetal (0.073 g, 0.6 mmol) were taken in toluene (20 mL) and this mixture was refluxed with stirring for 12 h. The reaction was cooled to a temperature of about 20-35° C., concentrated under reduced pressure and diluted with water (15 mL). The aqueous mass thus obtained was then extracted with ethyl acetate (3×25 mL). The combined organic layer was washed with brine, dried over sodium sulfate and was concentrated under reduced pressure to get the crude product. The crude product was purified by column chromatography using 60-120 mesh silica gel and about 30% ethyl acetate in petroleum ether as eluent to obtain the pure product as a yellow gum (0.2 g). MS (ESI): 701 (M+1)$^+$ Example 6

Synthesis of 3-(((5-(1H-pyrazol-3-yl)pyrimidin-2-yl)(3,5-bis(trifluoromethyl)benzyl)amino)methyl)-N,N-bis(cyclopropylmethyl)-7,7-dimethyl-6,7-dihydro-5H-cyclopenta[b]pyridin-2-amine

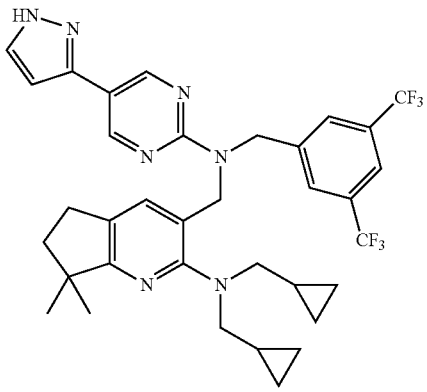 [SMILES: CC1(C)CCc2cc(CN(Cc3cc(C(F)(F)F)cc(C(F)(F)F)c3)c3ncc(-c4ccon4)cn3)c(N(CC3CC3)CC3CC3)nc21]

A mixture of (E)-1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5-yl)-3-(dimethylamino)prop-2-en-1-one (0.1 g, 0.1 mmol), obtained in Example 5, and hydrazine hydrate (0.03 g, 0.6 mmol) in ethanol (15 mL) was heated at about 70-75° C. with stirring for about 2 h. The mixture was concentrated under reduced pressure, diluted with water (10 mL) and the aqueous mass thus obtained was extracted with ethyl acetate (3×15 mL). The combined organic layer was washed with brine, dried over sodium sulfate and concentrated under reduced pressure to obtain the crude product. The crude product was purified by column chromatography using 60-120 mesh silica gel and 30% ethyl acetate in petroleum ether as eluent to obtain the pure product as a light yellow paste (0.04 g).

$^1$H NMR (400 MHz, CDCl$_3$): δ 8.79 (d, J=4.7 Hz, 3H), 7.75-7.73 (dd, J=8.8 Hz, 4H), 7.64 (d, J=2.2 Hz, 1H), 6.57 (d, J=2.2 Hz, 1H), 5.34 (s, 2H), 4.97 (s, 2H), 2.9 (d, J=6.6 Hz, 4H), 2.70-2.67 (m, 2H), 0.89-0.82 (m, 2H), 0.32-0.27 (m, 4H), 0.07-0.01 (m, 4H). MS (ESI): 670 (M+1)$^+$.

Example 7

Synthesis of 3-(((3,5-bis(trifluoromethyl)benzyl)(5-(isoxazol-3-yl)pyrimidin-2-yl)amino)methyl)-N,N-bis(cyclopropylmethyl)-7,7-dimethyl-6,7-dihydro-5H-cyclopenta[b]pyridin-2-amine

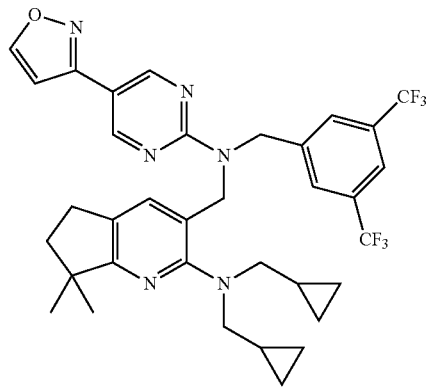

A mixture of (E)-1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5-yl)-3-(dimethylamino)prop-2-en-1-one (0.1 g, 0.1 mmol), obtained in Example 5 and hydroxylamine hydrochloride (0.03 g, 0.6 mmol) in methanol (15 mL) was heated at about 70-75° C. with stirring for about 2 h. The reaction was cooled to a temperature of about 20-35° C., diluted with water (10 mL) and the aqueous mass thus obtained was extracted with ethyl acetate (3×15 mL). The combined organic layer was washed with brine, dried over sodium sulfate and concentrated under reduced pressure to obtain the crude product. The crude was purified by column chromatography using 60-120 mesh silica gel and about 10% ethyl acetate in petroleum ether as eluent to obtain the pure product as a light yellow paste (0.03 g).

$^1$H NMR (400 MHz, CDCl$_3$): δ 8.66 (s, 2H), 8.03 (s, 1H), 7.73 (s, 1H), 7.26 (s, 1H), 6.65 (s, 1H), 5.36-5.34 (m, 2H), 5.08 (s, 2H), 4.86 (s, 2H), 2.97-2.96 (m, 4H), 2.69-2.67 (m, 2H), 1.93-1.89 (m, 2H), 1.29-1.22 (m, 6H), 0.94-0.80 (m, 2H), 0.31-0.27 (m, 4H), −0.01-0.04 (m, 4H).

MS (ESI): 671 (M+1)$^+$.

Example 8

Synthesis of 2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidine-5-carbonitrile

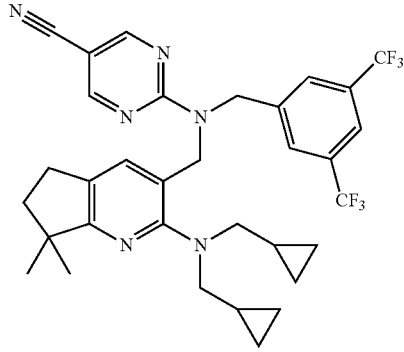 [SMILES: CC1(C)CCc2cc(CN(Cc3cc(C(F)(F)F)cc(C(F)(F)F)c3)c3ncc(C#N)cn3)c(N(CC3CC3)CC3CC3)nc21]

Toluene (5 mL) was added to a mixture of 3-(((3,5-bis(trifluoromethyl)benzyl)(5-bromopyrimidin-2-yl)amino)methyl)-N,N-bis(cyclopropylmethyl)-7,7-dimethyl-6,7-dihydro-5H-cyclopenta[b]pyridin-2-amine (0.02 g, 0.03 mmol), obtained in step 6 of Example 1, Zn(CN)$_2$ (0.003 g, 0.03 mmol), Pd(PPh$_3$)$_4$ (0.01 g, 0.008 mmol) and K$_2$CO$_3$ (0.008 g, 0.06 mmol) in a sealed tube. The above mixture was degassed with argon and heated to about 150° C. The mixture was stirred at the same temperature for about 2 days. The reaction mass was cooled to a temperature of about 20-35° C., water (10 mL) was added and the aqueous layer was extracted with ethyl acetate (2×30 mL). The combined organic layer was washed with brine, dried over sodium sulfate and concentrated under reduced pressure to get the desired product. MS (ESI): 629 (M+1)$^+$ Example 9

Synthesis of 2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidine-5-carboxamide

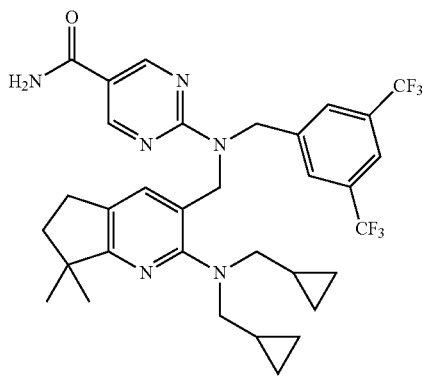 [SMILES: CC1(C)CCc2cc(CN(Cc3cc(C(F)(F)F)cc(C(F)(F)F)c3)c3ncc(C(N)=O)cn3)c(N(CC3CC3)CC3CC3)nc21]

A solution of potassium hydroxide (0.018 g, 0.3 mmol) in water (1.0 mL) was added to 2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidine-5-carbonitrile (0.02 g, 0.32 mmol, obtained in Example 8, in Ethanol (5 mL) followed by addition of hydrogen peroxide (0.02 mL) at about 20-35° C. The reaction mixture was heated to about 40° C. and was stirred at the same temperature for about 2 h.

The reaction mixture was cooled to about 20-35° C., water was added to it and the aqueous mass was extracted with ethyl acetate (3×15 mL). The combined organic layer was washed with brine, dried over sodium sulfate and filtered off. The filtrated was concentrated under reduced pressure to obtain the crude product which was purified by column chromatography and eluted with 50% ethyl acetate in petroleum ether.

$^1$H NMR (400 MHz, CDCl$_3$): δ 8.80 (s, 2H), 7.74 (s, 3H), 7.18 (s, 1H), 5.09 (s, 2H), 4.88 (s, 2H), 2.97 (d, J=6.6 Hz, 4H), 2.69 (t, J=7.3 Hz, 2H), 1.92 (t, J=6.4 Hz, 2H), 1.22 (s, 6H), 0.85-0.82 (m, 2H), 0.30-0.28 (m, 4H), 0.01-0.008 (m, 4H). MS (ESI): 647 (M+1)$^+$.

Example 10

Synthesis of 3-(((3,5-bis(trifluoromethyl)benzyl)(5-morpholinopyrimidin-2-yl)amino)methyl)-N,N-bis(cyclopropylmethyl)-7-methyl-6,7-dihydro-5H-cyclopenta[b]pyridin-2-amine

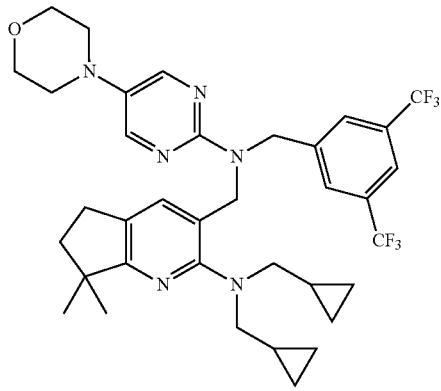 [SMILES: CC1(C)CCc2cc(CN(Cc3cc(C(F)(F)F)cc(C(F)(F)F)c3)c3ncc(N4CCOCC4)cn3)c(N(CC3CC3)CC3CC3)nc21]

3-(((3,5-bis(trifluoromethyl)benzyl)(5-morpholinopyrimidin-2-yl)amino)methyl)-N,N-bis(cyclopropylmethyl)-7-methyl-6,7-dihydro-5H-cyclopenta[b]pyridin-2-amine was prepared from 2-methylcyclopentanone by following substantially similar procedure as described in Example 3 and employing appropriate materials and reagents.

$^1$H NMR (400 MHz, CDCl$_3$): δ 8.15 (s, 2H), 7.70 (s, 2H), 7.69 (s, 2H), 7.21 (s, 1H), 5.08-4.72 (m, 4H), 3.88-3.86 (m, 4H), 3.13-3.04 (m, 4H), 2.73-2.67 (m, 2H), 2.36-2.28 (m, 2H), 1.21 (d, J=7.0 Hz, 3H), 0.86-0.81 (m, 2H), 0.33-0.27 (m, 4H), 0.01-0.005 (m, 4H). MS (ESI): 675 (M+1)$^+$.

Example 11

Synthesis of 3-(((3,5-bis(trifluoromethyl)benzyl)(5-morpholinopyrimidin-2-yl)amino)methyl)-N,N-bis(cyclopropylmethyl)-8-methyl-5,6,7,8-tetrahydroquinolin-2-amine

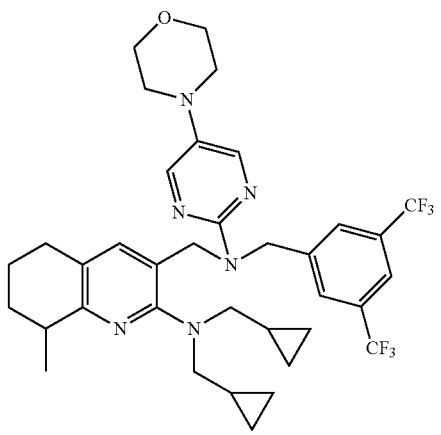 [SMILES: CC1CCCc2cc(CN(Cc3cc(C(F)(F)F)cc(C(F)(F)F)c3)c3ncc(N4CCOCC4)cn3)c(N(CC3CC3)CC3CC3)nc21]

3-(((3,5-bis(trifluoromethyl)benzyl)(5-morpholinopyrimidin-2-yl)amino)methyl)-N,N-bis(cyclopropylmethyl)-8-methyl-5,6,7,8-tetrahydroquinolin-2-amine was prepared from 2-methylcyclohexanone by following substantially similar procedure as described in Example 3 and employing appropriate materials and reagents.

¹H NMR (400 MHz, CDCl₃): δ 7.73 (s, 1H), 7.70 (s, 2H), 7.27 (s, 1H), 4.83 (s, 2H), 4.65 (s, 2H), 4.18 (s, 3H), 2.94 (d, J=5.1 Hz, 4H), 2.70 (t, J=6.4 Hz, 2H), 1.92 (t, J=7.3 Hz, 2H), 1.56 (s, 6H), 0.79-0.75 (m, 2H), 0.29-0.25 (m, 4H), 0.02-0.006 (m, 4H). MS (ESI): 608 (M+1)⁺

Example 12

Synthesis of 3-(((3,5-bis(trifluoromethyl)benzyl)(2H-tetrazol-5-yl)amino)methyl)-N,N-bis(cyclopropylmethyl)-7,7-dimethyl-6,7-dihydro-5H-cyclopenta[b]pyridin-2-amine

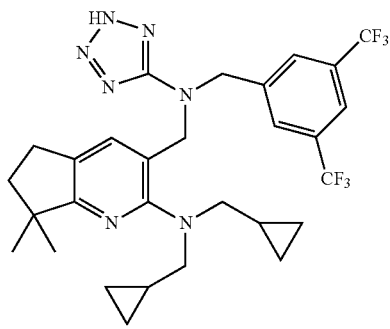 [SMILES: CC1(C)CCc2cc(CN(Cc3cc(C(F)(F)F)cc(C(F)(F)F)c3)c3nn[nH]n3)c(N(CC3CC3)CC3CC3)nc21]

Step 1: Synthesis of N-((2-(bis(cyclopropylmethyl)amino)-7,7-dimethyl-6,7-dihydro-5H-cyclopenta[b]pyridin-3-yl)methyl)-N-(3,5-bis(trifluoromethyl)benzyl)cyanamide

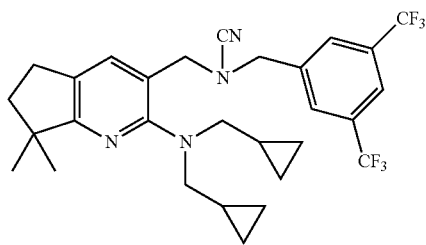 [SMILES: CC1(C)CCc2cc(CN(C#N)Cc3cc(C(F)(F)F)cc(C(F)(F)F)c3)c(N(CC3CC3)CC3CC3)nc21]

To 3-(((3,5-bis(trifluoromethyl)benzylamino)methyl)-N,N-bis(cyclopropylmethyl)-7,7-dimethyl-6,7-dihydro-5H-cyclopenta[b]pyridin-2-amine (0.3 g, 0.57 mmol), obtained in step-5 of Example-1, in methanol (8 ml) were added CNBr (0.074 g, 0.6 mmol) followed by addition of sodium hydrogen carbonate (0.1 g, 1.2 mmol). The reaction mixture was stirred at about 20-35° C. for about 2 h. The reaction mixture was concentrated under reduced pressure and diluted the residue with water (15 ml). The aqueous mass thus obtained was then extracted with ethyl acetate (3×25 ml). The combined organic layer was washed with brine, dried over sodium sulfate and concentrated under reduced pressure to obtain the crude product (0.3 g). MS (ESI): 551 (M+1)⁺

Step 2: Synthesis of 3-(((3,5-bis(trifluoromethyl)benzyl)(2H-tetrazol-5-yl)amino)methyl)-N,N-bis(cyclopropylmethyl)-7,7-dimethyl-6,7-dihydro-5H-cyclopenta[b]pyridin-2-amine

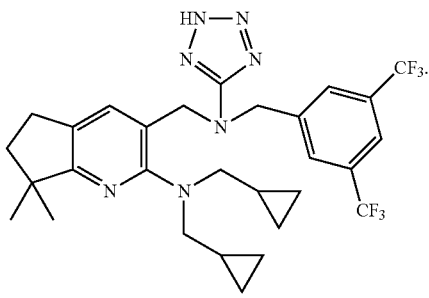 [SMILES: CC1(C)CCc2cc(CN(Cc3cc(C(F)(F)F)cc(C(F)(F)F)c3)c3nn[nH]n3)c(N(CC3CC3)CC3CC3)nc21]

To a solution of N-((2-(bis(cyclopropylmethyl)amino)-7,7-dimethyl-6,7-dihydro-5H-cyclopenta[b]pyridin-3-yl)methyl)-N-(3,5-bis(trifluoromethyl)benzyl)cyanamide (0.3 g, 0.00054 mmol) obtained in step-1, in DMF (5 ml) were added NaN₃ (0.18 g, 2.7 mmol) and ammonium chloride (0.15 g, 2.7 mmol) was heated at 100° C. with stirring for about 2 h.

The reaction mixture was cooled to about 20-35° C., water was added to it and the aqueous mass was extracted with ethyl acetate (3×15 mL). The combined organic layer was washed with brine, dried over sodium sulfate and filtered off. The filtrate was dried under vacuum to obtain the crude which was purified by column chromatography using 60-120 mesh silica gel and 40% ethyl acetate in petroleum ether as eluent to obtain the pure product (0.3 g).

¹H NMR (400 MHz, CDCl₃): δ 7.82 (s, 1H), 7.75 (s, 2H), 6.99 (s, 1H), 5.04 (s, 2H), 4.43 (s, 2H), 3.21 (d, J=6.9 Hz, 2H), 2.71 (t, J=7.4 Hz, 2H), 1.96 (t, J=7.2 Hz, 2H), 1.22 (s, 6H), 0.95-0.88 (m, 4H), 0.19-0.06 (m, 4H). MS (ESI): 594 (M+1)⁺

Example 13

Synthesis of 3-(((3,5-bis(trifluoromethyl)benzyl)(2-methyl-2H-tetrazol-5-yl)amino)methyl)-N,N-bis(cyclopropylmethyl)-7,7-dimethyl-6,7-dihydro-5H-cyclopenta[b]pyridin-2-amine

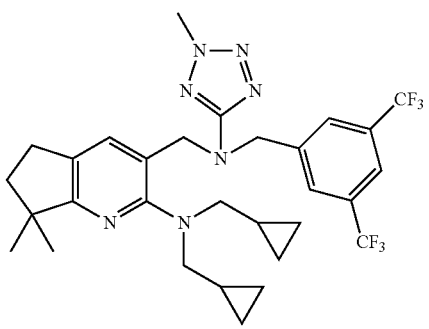 [SMILES: Cn1nnc(N(Cc2cc(C(F)(F)F)cc(C(F)(F)F)c2)Cc2cc3c(nc2N(CC2CC2)CC2CC2)C(C)(C)CC3)n1]

To a suspension of 3-(((3,5-bis(trifluoromethyl)benzyl)(2H-tetrazol-5-yl)amino)methyl)-N,N-bis(cyclopropylmethyl)-7,7-dimethyl-6,7-dihydro-5H-cyclopenta[b]pyridin-2-amine (0.3 g, 0.44 mmol), obtained in Example 12, in DCM:H₂O (5 ml; 4:1 ratio) were added NaOH (0.035 g, 8.7 mmol), TBAB (0.01 g, 2 mmol) and dimethyl sulfate (0.06 ml, 5.3 mmol). The reaction mixture was stirred at about 20-35° C. for about 30 min.

Water was added to it and the aqueous mass was extracted with ethyl acetate (3×15 mL). The combined organic layer was washed with brine, dried over sodium sulfate and filtered off. The filtrate was dried under reduced pressure to obtain the crude product which was purified by column chromatography using 60-120 mesh silica gel and 5% ethyl acetate in petroleum ether as eluent to afford the pure product as a yellow gum (0.1 gram, 45%).

$^1$H NMR (400 MHz, CDCl$_3$): δ 7.73 (s, 1H), 7.70 (s, 2H), 7.27 (s, 1H), 4.83 (s, 2H), 4.65 (s, 2H), 4.18 (s, 3H), 2.94 (d, J=5.1 Hz, 4H), 2.70 (t, J=6.4 Hz, 2H), 1.92 (t, J=7.3 Hz, 2H), 1.56 (s, 6H), 0.79-0.75 (m, 2H), 0.29-0.25 (m, 4H), 0.02-0.006 (m, 4H). MS (ESI): 608 (M+1)$^+$.

Example 14

Synthesis of 3-(((3,5-bis(trifluoromethyl)benzyl)(2-isopropyl-2H-tetrazol-5-yl)amino)methyl)-N,N-bis(cyclopropylmethyl)-7,7-dimethyl-6,7-dihydro-5H-cyclopenta[b]pyridin-2-amine

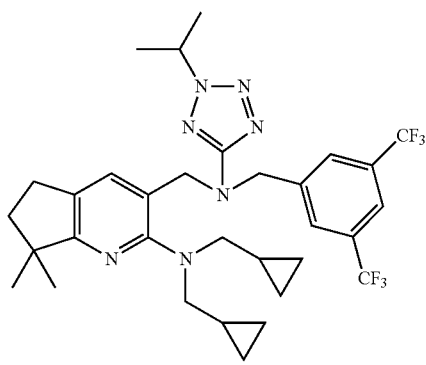 [SMILES: CC(C)n1nnc(N(Cc2cc(C(F)(F)F)cc(C(F)(F)F)c2)Cc2cc3c(nc2N(CC2CC2)CC2CC2)C(C)(C)CC3)n1]

To a stirred solution of NaH (0.002 g, 0.03 mmol) in DMF (5 mL) were added 3-(((3,5-bis(trifluoromethyl)benzyl)(2H-tetrazol-5-yl)amino)methyl)-N,Nbis(cyclopropylmethyl)-7,7-dimethyl-6,7-dihydro-5H-cyclopenta[b]pyridin-2-amine (0.002 g, 0.03 mmol), obtained in Example 12, followed by the addition of 2-bromo propane (0.005 mg, 0.3 mmol) at 0° C. and continued stirring at about 20-35° C. for about 12-16 h.

Ice cold water was added to it and the aqueous mass was extracted with ethyl acetate (3×15 mL). The combined organic layer was washed with brine, dried over sodium sulfate and filtered off. The filtrate was dried under vacuum to obtain the crude product which was purified by column chromatography using 100-200 mesh silica gel and about 10% acetone in petroleum ether as eluent to afford the pure product as a yellow gum (0.01 g).

$^1$H NMR (400 MHz, CDCl$_3$): δ 7.74-7.73 (m, 3H), 7.32 (s, 1H), 4.84 (s, 2H), 4.63 (s, 2H), 2.96 (d, J=6.6 Hz, 4H), 2.71 (t, J=7.1 Hz, 2H), 2.30-2.24 (m, 1H), 1.93 (t, 7.1 Hz, 2H), 1.60 (d, J=7.0 Hz, 6H), 1.22 (s, 6H), 0.83-0.80 (m, 2H), 0.31-0.26 (m, 4H), 0.01-0.006 (m, 4H).

MS (ESI): 636 (M+1)$^+$.

Example 15

3-(((3,5-bis(trifluoromethyl)benzyl)(2-isobutyl-2H-tetrazol-5-yl)amino)methyl)-N,N-bis(cyclo propylmethyl)-7,7-dimethyl-6,7-dihydro-5H-cyclopenta[b]pyridin-2-amine

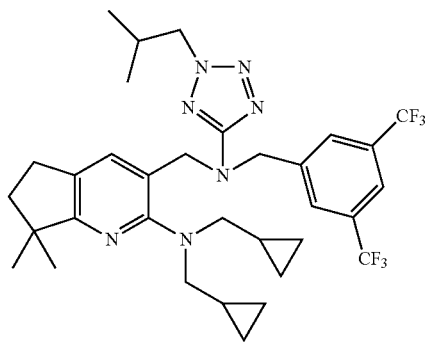 [SMILES: CC(C)Cn1nnc(N(Cc2cc(C(F)(F)F)cc(C(F)(F)F)c2)Cc2cc3c(nc2N(CC2CC2)CC2CC2)C(C)(C)CC3)n1]

To a stirred solution of NaH (0.036 g, 0.15 mmol) in DMF (5 ml) were added 3-(((3,5-bis(trifluoromethyl)benzyl)(2H-tetrazol-5-yl)amino)methyl)-N,Nbis(cyclopropylmethyl)-7,7-dimethyl-6,7-dihydro-5H-cyclopenta[b]pyridin-2-amine (0.09 g, 0.15 mmol), obtained in Example 12, followed by the addition of 1-bromo-2-methylpropane (0.041 mg, 0.3 mmol) at 0° C. and continued stirring at about 20-35° C. for about 12-16 h.

Ice cold water was added to it and the aqueous mass was extracted with ethyl acetate (3×15 mL). The combined organic layer was washed with brine, dried over sodium sulfate and filtered off. The filtrate was dried under vacuum to obtain the crude product which was purified by column chromatography using 100-200 mesh silica gel and 4% ethyl acetate in petroleum ether as eluent to obtain the pure product as a yellow gum (0.03 g).

$^1$H NMR (400 MHz, CDCl$_3$): δ 7.72-7.71 (m, 3H), 7.30 (s, 1H), 4.84 (s, 2H), 4.65 (s, 2H), 4.94 (d, 6.3 Hz, 2H), 2.95 (d, J=6.6 Hz, 4H), 2.70 (t, J=7.1 Hz, 2H), 2.30-2.29 (m, 1H), 1.92 (t, J=7.1 Hz, 2H), 1.22 (s, 6H), 0.94 (d, J=6.6 Hz, 6H), 0.82-0.78 (m, 2H), 0.30-0.26 (m, 4H), 0.01-0.03 (m, 4H). MS (ESI): 650 (M+1)$^+$.

Example 16

Synthesis of 3-(((3,5-bis(trifluoromethyl)benzyl)(2-methyl-2H-tetrazol-5-yl)amino)methyl)-N,N-bis(cyclopropylmethyl)-8,8-dimethyl-5,6,7,8-tetrahydroquinolin-2-amine

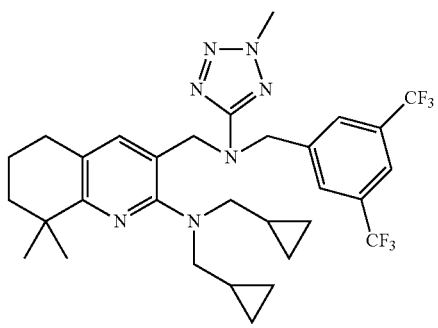 [SMILES: Cn1nnc(N(Cc2cc(C(F)(F)F)cc(C(F)(F)F)c2)Cc2cc3c(nc2N(CC2CC2)CC2CC2)C(C)(C)CCC3)n1]

3-(((3,5-bis(trifluoromethyl)benzyl)(2-methyl-2H-tetrazol-5-yl)amino)methyl)-N,N-bis(cyclopropylmethyl)-8,8-dimethyl-5,6,7,8-tetrahydroquinolin-2-amine was prepared from 2,2-dimethylcyclohexanone by substantially following the procedure as described in Example 13 and employing appropriate materials and reagents.

$^1$H NMR (400 MHz, CDCl$_3$): δ 7.73 (s, 1H), 7.70 (s, 2H), 7.09 (s, 1H), 4.77 (s, 2H), 4.66 (s, 2H), 4.18 (s, 3H), 2.93 (d, J=6.6 Hz, 4H), 2.57 (t, J=6.1 Hz, 2H), 1.69-1.57 (m, 4H), 1.25 (s, 6H), 0.89-0.77 (m, 2H), 0.89-0.77 (m, 2H), 0.31-0.26 (m, 4H), 0.02-0.15 (m, 4H).

MS (ESI): 622 (M+1)$^+$.

Example 17

6-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)benzo[d]oxazol-2(3H)-one

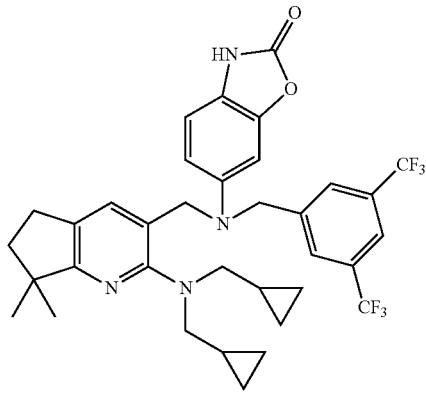 [SMILES: CC1(C)CCc2cc(CN(Cc3cc(C(F)(F)F)cc(C(F)(F)F)c3)c3ccc4[nH]c(=O)oc4c3)c(N(CC3CC3)CC3CC3)nc21]

Step 1: 6-(((2-(bis(cyclopropylmethyl)amino)-7,7-dimethyl-6,7-dihydro-5H-cyclopenta[b]pyridine-3-yl)methyl)amino)benzo[d]oxazol-2(3H)-one

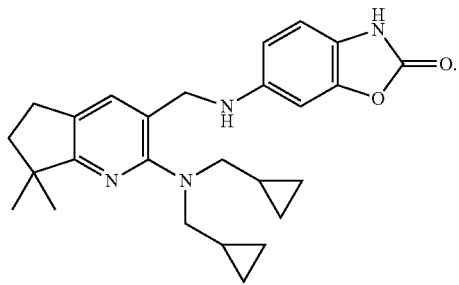 [SMILES: CC1(C)CCc2cc(CNc3ccc4[nH]c(=O)oc4c3)c(N(CC3CC3)CC3CC3)nc21]

To a solution of 2-(bis(cyclopropylmethyl)amino)-7,7-dimethyl-6,7-dihydro-5H-cyclopenta[b]pyridine-3-carbaldehyde (0.2 g, 0.671 mmol, obtained in step 4 of Example-1, and 6-aminobenzo[d]oxazol-2(3H)-one (0.1 g, 0.671 mmol) in methanol (10 mL), was added glacial acetic acid (0.3 mL) and the resulting mixture was stirred for 15 min at a temperature of about 20-35° C. Sodium cyanoborohydride (0.042 g, 0.671 mmol) was added portion wise to this reaction mixture and the reaction mixture was stirred for about 3 h.

After evaporating solvent from the mixture under reduced pressure, it was extracted with water (30 mL) and dichloromethane (2×30 mL). The organic layer was collected, washed with brine, dried over sodium sulfate and concentrated under reduced pressure to obtain the crude product. The crude product was purified by column chromatography using silica gel (60-120 mesh) and eluted with about 50% petroleum ether in ethyl acetate to obtain the pure product as a pale yellow liquid (0.15 g). MS (ESI): 433 (M+1)$^+$ Step-2: 6-(((2-(bis(cyclopropylmethyl)amino)-7,7-dimethyl-6,7-dihydro-5H-cyclopenta[b]pyridine-3-yl)methyl)(3,5-bis(trifluoromethyl)benzyl)amino)benzo[d]oxazol-2(3H)-one

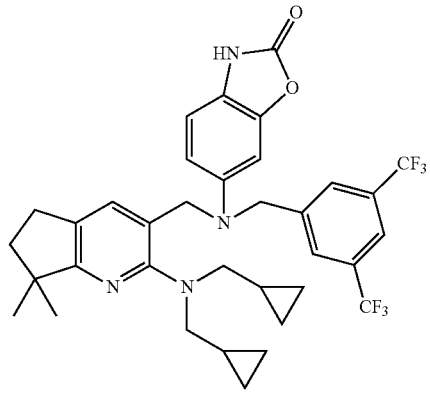 [SMILES: CC1(C)CCc2cc(CN(Cc3cc(C(F)(F)F)cc(C(F)(F)F)c3)c3ccc4[nH]c(=O)oc4c3)c(N(CC3CC3)CC3CC3)nc21]

To a solution of 6-(((2-(bis(cyclopropylmethyl)amino)-7,7-dimethyl-6,7-dihydro-5H-cyclopenta[b]pyridin-3-yl)methyl)amino)benzo[d]oxazol-2(3H)-one (0.15 g, 0.346 mmol) obtained in the above step-1, in THF (10 ml) were added 1-(bromomethyl)-3,5-bis(trifluoromethyl)benzene (0.106 g, 0.346 mmol), sodium hydrogen carbonate (0.043 g, 0.519 mmol) was stirred at about 20-35° C. for about 14 h.

Water was added to it and the aqueous mass was extracted with ethyl acetate (3×15 mL). The combined organic layer was washed with brine, dried over sodium sulfate and filtered off. The filtrate was dried under vacuum to obtain the crude product which was purified by column chromatography using 60-120 mesh silica gel and 30% ethyl acetate in petroleum ether as eluent to achieve the pure product (0.06 g).

$^1$HNMR (400 MHz, CDCl$_3$): δ7.78 (s, 2H), 7.69 (s, 2H), 7.26 (s, 1H), 6.81 (d, J=8.8 Hz, 1H), 6.57 (s, 1H), 6.42 (d, J=2.4 Hz, 1H), 4.72 (s, 2H), 4.68 (s, 2H), 2.96 (d, J=6.8 Hz, 3H), 2.71 (t, J=6.8 Hz, 2H), 1.92 (t, J=7.2 Hz, 2H), 1.22 (s, 9H), 0.88-0.83 (m, 2H), 0.34-0.29 (m, 4H), 0.0034-0.0001 (m, 4H). MS (ESI): 659 (M+1)$^+$.

Example 18

Synthesis of 3-(((3,5-bis(trifluoromethyl)benzyl)(2-methyl-2H-tetrazol-5-yl)amino)methyl)-N,N-bis(cyclopropylmethyl)-7-methyl-6,7-dihydro-5H-cyclopenta[b]pyridin-2-amine

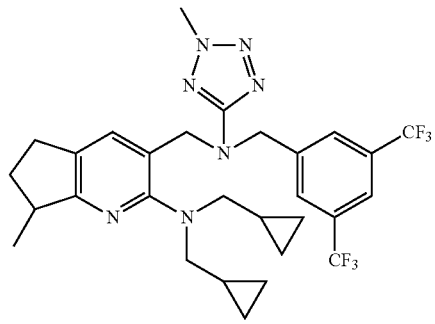 [SMILES: CC1CCc2cc(CN(Cc3cc(C(F)(F)F)cc(C(F)(F)F)c3)c3nnn(C)n3)c(N(CC3CC3)CC3CC3)nc21]

3-(((3,5-bis(trifluoromethyl)benzyl)(2-methyl-2H-tetrazol-5-yl)amino)methyl)-N,N-bis(cyclopropylmethyl)-7-methyl-6,7-dihydro-5H-cyclopenta[b]pyridin-2-amine was prepared from 2-methylcyclopentanone by following substantially similar procedure as described in Example 13 and employing appropriate materials and reagents.

$^1$H NMR (400 MHz, CDCl$_3$): δ 7.72 (s, 1H), 7.68 (s, 2H), 7.28 (s, 1H), 4.84 (s, 2H), 4.66 (s, 2H), 3.96 (s, 3H), 3.11-3.00 (m, 4H), 3.09-2.88 (m, 4H), 2.75-2.68 (m, 2H), 2.33-2.32 (m, 2H), 1.26 (d, J=6.9 Hz, 3H), 0.89-0.79 (m, 4H), 0.3-0.28 (m, 4H). MS (ESI): 594 (M+1)$^+$.

Example 19

Determination of In Vitro Activity Using Fluorometric Technique

An in vitro cholesteryl ester transfer protein inhibition (CETP) assay using a commercially available fluorometric assay kit from ROAR Biomedicals, USA was used to measure the CETP inhibition activity of the compounds of this application. This assay kit uses a donor molecule containing a fluorescent self-quenched neutral lipid that is transferred to an acceptor molecule in the presence of CETP enzyme. The CETP-mediated transfer of the fluorescent neutral lipid to the acceptor molecule results in an increase in fluorescence (Excitation: 492 nm; Emission: 516 nm).

A 20 mM stock solution of compounds were prepared in 100% DMSO and further dilutions were made such that the final concentration of DMSO in the reaction mix was 1%. The reactions were performed as suggested by the kit manufacturer as follows. The assay was performed in 96 well microplates and in each well, the reaction mixture contained 190 µl of assay buffer (150 mM NaCl, 10 mM Tris and 2 mM EDTA, pH-7.4), 4 µl of donor particle, 4 lA of acceptor particle, rCETP (50 ng) and 2 µl of test compound at varying final concentration of 0.1, 1, 10, 100, 1000 & 10000 nM. Two control reactions were performed, one without test compound (positive control) and the other without the rCETP (negative control). The reactions were incubated at 37° C. for 90 minutes and the reaction plate was transferred to a PCR machine MX3005P and the fluorescence units (FLU) were quantified (Excitation: 492 nm; Emission: 516 nm).

The negative control values were subtracted from the positive control as well as all the test values to correct for background fluorescence. The percentage inhibition of activity is calculated by using the following equation:

% Inhibition of CETP activity=[100−(100×(FLU in test/FLU in positive control))].

The half maximal inhibitory concentration (IC$_{50}$) was determined using the BIOGRAPH software (version no. 3.3).

Using this protocol, various compounds as described herein were found to exhibit inhibitory effect on CETP as follows:

| Example No. | IC$_{50}$ (nM) |
| --- | --- |
| 2 | ~29 |
| 3 | ~20 |
| 4 | ~50 |
| 6 | ~29 |
| 7 | ~33 |
| 9 | ~94 |
| 10 | ~90 |
| 11 | ~40 |
| 17 | ~16 |

Although the invention as disclosed in the present application has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound having the formula (I), or a stereoisomer thereof or a pharmaceutically acceptable salt thereof:

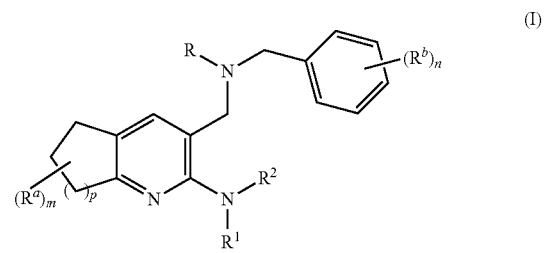

(I)

wherein,

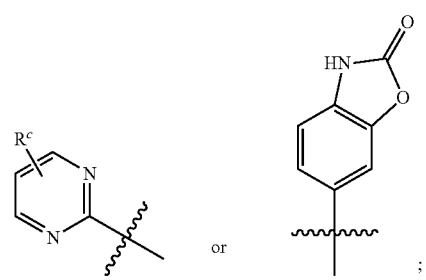

R represents

R$^1$ and R$^2$ are independently selected from hydrogen, acyl, haloalkyl, —(CHR$^e$)$_q$R$^3$, an optionally substituted group selected from alkyl or cycloalkyl, wherein optional substituent, in each occurrence, is independently selected from halogen, cyano, hydroxyl, an alkyl, a haloalkyl or an alkoxy;

R$^3$ is a group selected from alkoxy, haloalkoxy, cycloalkyl, aryl, heterocyclyl or heteroaryl, wherein R$^3$ is optionally substituted with a group selected from halogen, cyano, hydroxyl, alkyl, haloalkyl or alkoxy;

R$^a$, in each occurrence, is independently selected from cyano, hydroxy, alkyl, haloalkyl or alkoxy;

R$^b$, in each occurrence, is independently selected from halogen, alkyl, haloalkyl, hydroxy, alkoxy or haloalkoxy;

R$^c$ is independently selected from hydrogen, cyano, halogen, —C(=O)—R$^f$, —CONR$^g$R$^h$, —C(=O)—CH=CH—NR$^i$R$^j$, an optionally substituted group selected from cycloalkyl, aryl, heteroaryl or heterocyclyl ring, wherein the optional substituent, in each occurrence, is selected independently from hydrogen, halogen, cyano, hydroxyl, alkyl, haloalkyl, alkoxy, alkoxyalkyl or haloalkoxy;

R$^e$, in each occurrence, is independently selected from hydrogen, alkyl or alkoxy;

R$^f$, is hydrogen or alkyl;

R$^g$, R$^h$, R$^i$ and R$^j$ are independently represent hydrogen or alkyl;

m is 0, 1 or 2;

n is 0, 1, 2 or 3;
p is 1 or 2; and
q is 0, 1, 2, 3, 4 or 5.

2. The compound according to claim 1 having the formula (Ib):

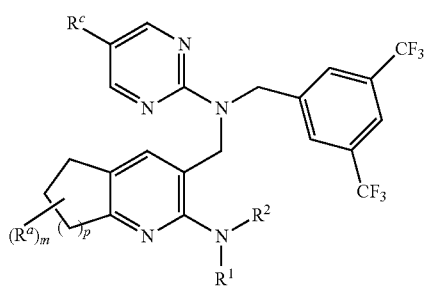

or a stereoisomer thereof or a pharmaceutically acceptable salt thereof; wherein, $R^1$ and $R^2$ are selected, independently, from hydrogen or —(CHR$^e$)$_q$R$^3$;

$R^3$ represents cycloalkyl, aryl, heterocyclyl or heteroaryl;

$R^e$ represents optionally substituted heterocyclic ring selected from:

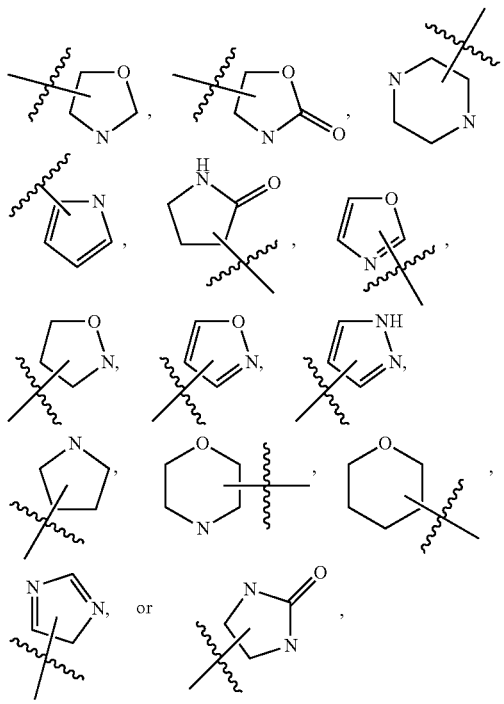

wherein the optional substituent is selected from halogen, cyano, hydroxyl, alkyl, haloalkyl, alkoxy, alkoxyalkyl or haloalkoxy;

q represents 1, 2 or 3; and
p represents 1 or 2.

3. The compound according to claim 2, having the formula (Ic)

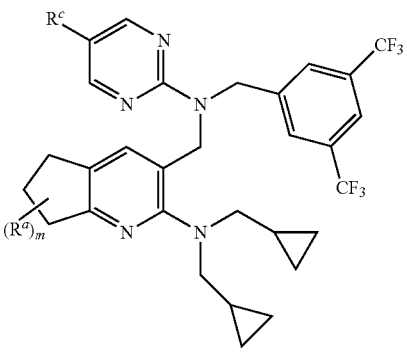

or a stereoisomer thereof or a pharmaceutically acceptable salt thereof wherein, $R^c$ represents

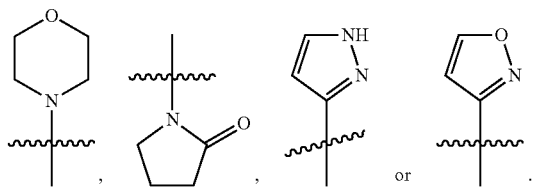 [SMILES: *N1CCOCC1 ; *N1CCCC1=O ; *c1cc[nH]n1 ; *c1ccon1]

4. A compound having the formula (Id)

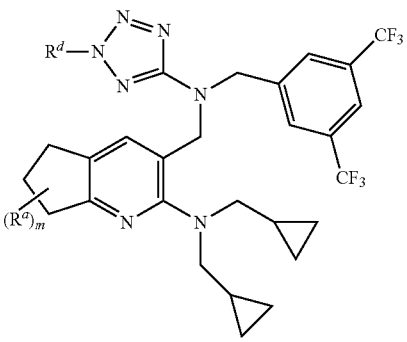

or a stereoisomer thereof or a pharmaceutically acceptable salt thereof.

5. The compound according to claim 1, having the formula (Ie)

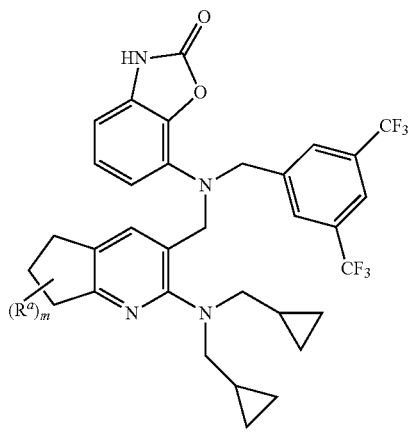

or a stereoisomer thereof or a pharmaceutically acceptable salt thereof.

6. A compound selected from the group consisting of:

3-(((3,5-bis(trifluoromethyl)benzyl)(5-bromopyrimidin-2-yl)amino)methyl)-N,N-bis(cyclopropylmethyl)-7,7-dimethyl-6,7-dihydro-5H-cyclopenta[b]pyridin-2-amine;

1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5H-yl)pyrrolidin-2-one;

3-(((3,5-bis(trifluoromethyl)benzyl)(5-morpholinopyrimidin-2-yl)amino)methyl)-N,N-bis(cyclopropylmethyl)-7,7-dimethyl-6,7-dihydro-5H-cyclopenta[b]pyridin-2-amine;

1-(2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidin-5H-yl)ethanone;

(E)-1-(2-(((2-(bis(cyclopropylmethyl)amino)-7,7-dimethyl-6,7-dihydro-5H-cyclopenta[b]pyridine-3-yl)methyl)(3,5-bis(trifluoromethyl)benzyl)amino)pyrimidin-5H-yl)-3-(dimethyl amino)prop-2-en-1-one;

(E)-1-(2-(((2-(bis(cyclopropylmethyl)amino)-7,7-dimethyl-6,7-dihydro-5H-cyclopenta[b]pyridine-3-yl)methyl)(3,5-bis(trifluoromethyl)benzyl)amino)pyrimidin-5-yl)-3-(dimethylamino)prop-2-en-1-one;

3-(((3,5-bis(trifluoromethyl)benzyl)(5-(isoxazol-3-yl)pyrimidin-2-yl)amino)methyl)-N,N-bis(cyclopropylmethyl)-7,7-dimethyl-6,7-dihydro-5H-cyclopenta[b]pyridin-2-amine;

2-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)pyrimidine-5-carbonitrile;

2-(((2-(bis(cyclopropylmethyl)amino)-7,7-dimethyl-6,7-dihydro-5H-cyclopenta[b]pyridine-3-yl)methyl)(3,5-bis(trifluoromethyl)benzyl)amino)pyrimidine-5-carboxamide;

3-(((3,5-bis(trifluoromethyl)benzyl)(5-morpholinopyrimidin-2-yl)amino)methyl)-N,N-bis(cyclopropylmethyl)-7-methyl-6,7-dihydro-5H-cyclopenta[b]pyridin-2-amine;

3-(((3,5-bis(trifluoromethyl)benzyl)(5-morpholinopyrimidin-2-yl)amino)methyl)-N,N-bis(cyclopropylmethyl)-8-methyl-5,6,7,8-tetrahydroquinolin-2-amine;

3-(((3,5-bis(trifluoromethyl)benzyl)(2H-tetrazol-5H-yl)amino)methyl)-N,N-bis(cyclopropylmethyl)-7,7-dimethyl-6,7-dihydro-5H-cyclopenta[b]pyridin-2-amine;

3-(((3,5-bis(trifluoromethyl)benzyl)(2-methyl-2H-tetrazol-5-yl)amino)methyl)-N,N-bis(cyclopropylmethyl)-7,7-dimethyl-6,7-dihydro-5H-cyclopenta[b]pyridin-2-amine;

3-(((3,5-bis(trifluoromethyl)benzyl)(2-isopropyl-2H-tetrazol-5-yl)amino)methyl)-N,N-bis(cyclopropylmethyl)-7,7-dimethyl-6,7-dihydro-5H-cyclopenta[b]pyridin-2-amine;

3-(((3,5-bis(trifluoromethyl)benzyl)(2-isobutyl-2H-tetrazol-5-yl)amino)methyl)-N,N-bis(cyclopropylmethyl)-7,7-dimethyl-6,7-dihydro-5H-cyclopenta[b]pyridin-2-amine;

3-(((3,5-bis(trifluoromethyl)benzyl)(2-methyl-2H-tetrazol-5-yl)amino)methyl)-N,N-bis(cyclopropylmethyl)-8,8-dimethyl-5,6,7,8-tetrahydroquinolin-2-amine;

6-(((2-(bis(cyclopropylmethyl)amino)-7,7-dimethyl-6,7-dihydro-5H-cyclopenta[b]pyridin-3-yl)methyl)(3,5-bis(trifluoromethyl)benzyl)amino)benzo[d]oxazol-2(3H)-one;

3-(((5-(1H-pyrazol-3-yl)pyrimidin-2-yl)(3,5-bis(trifluoromethyl)benzyl)amino)methyl)-N,N-bis(cyclopropylmethyl)-7,7-dimethyl-6,7-dihydro-5H-cyclopenta[b]pyridin-2-amine; and 3-(((3,5-bis(trifluoromethyl)benzyl)(2-methyl-2H-tetrazol-5-yl)amino)methyl)-N,N-bis(cyclopropylmethyl)-7-methyl-6,7-dihydro-5H-cyclopenta[b]pyridin-2-amine;

or a stereoisomer thereof or a pharmaceutically acceptable salt thereof.

7. A pharmaceutical composition comprising at least one compound of formula (I) according to claim 1 and at least one pharmaceutically acceptable excipient.

8. A method of inhibiting cholesteryl ester-transfer protein (CETP) in a patient comprising administering to said patient a therapeutically effective amount of a compound of formula (I) according to claim 1.

9. A method of increasing high density lipoprotein (HDL) cholesterol in a patient comprising administering to said patient a therapeutically effective amount of a compound of formula (I) according to claim 1.

10. A method of lowering low density lipoprotein (LDL) cholesterol in a patient comprising administering to said patient a therapeutically effective amount of a compound of formula (I) according to claim 1.

11. A pharmaceutical composition comprising at least one compound of claim 6 or a stereoisomer thereof or a pharmaceutically acceptable salt thereof and at least one pharmaceutically acceptable excipient.

12. A method of inhibiting cholesteryl ester-transfer protein (CETP in a patient comprising administering to said patient a therapeutically effective amount of a compound according to claim 6.

13. A method of increasing high density lipoprotein (HDL) cholesterol in a patient comprising administering to said patient a therapeutically effective amount of a compound according to claim 6.

14. A method of lowering low density lipoprotein (LDL) cholesterol in a patient comprising administering to said patient a therapeutically effective amount of a compound according to claim 6.

* * * * *